US008962250B2

(12) United States Patent
Stanley

(10) Patent No.: US 8,962,250 B2
(45) Date of Patent: Feb. 24, 2015

(54) METHODS FOR THE AMPLIFICATION, QUANTITATION AND IDENTIFICATION OF NUCLEIC

(75) Inventor: Keith Stanley, Darlinghurst (AU)

(73) Assignee: Qiagen GmbH, Hilden (DE)

( * ) Notice: Subject to any disclaimer, the term of this patent is extended or adjusted under 35 U.S.C. 154(b) by 830 days.

(21) Appl. No.: 11/515,377

(22) Filed: Sep. 1, 2006

(65) Prior Publication Data

US 2007/0190540 A1    Aug. 16, 2007

Related U.S. Application Data

(60) Provisional application No. 60/713,636, filed on Sep. 1, 2005.

(30) Foreign Application Priority Data

Sep. 1, 2005   (AU) ............................... 2005205791
Apr. 5, 2006   (CA) .................................... 2545613

(51) Int. Cl.
*C12Q 1/68*       (2006.01)
*C12P 19/34*      (2006.01)

(52) U.S. Cl.
CPC ............... *C12Q 1/6844* (2013.01); *C12P 19/34* (2013.01); *C12Q 1/6851* (2013.01)
USPC ........................... 435/6.12; 435/6.1; 435/6.11

(58) Field of Classification Search
CPC ................................ C12Q 1/686; C12P 19/34
See application file for complete search history.

(56) References Cited

U.S. PATENT DOCUMENTS

| 4,683,195 | A  | 7/1987  | Mullis et al. |
| 4,683,202 | A  | 7/1987  | Mullis |
| 4,965,188 | A  | 10/1990 | Mullis et al. |
| 5,210,015 | A  | 5/1993  | Gelfand et al. |
| 5,436,134 | A  | 7/1995  | Haugland et al. |
| 5,487,972 | A  | 1/1996  | Gelfand et al. |
| 5,538,848 | A  | 7/1996  | Livak et al. |
| 5,658,751 | A  | 8/1997  | Yue et al. |
| 5,792,611 | A  | 8/1998  | Hamelin |
| 5,804,375 | A  | 9/1998  | Gelfand et al. |
| 5,994,056 | A  | 11/1999 | Higuchi |
| 6,030,787 | A  | 2/2000  | Livak et al. |
| 6,569,627 | B2 | 5/2003  | Wittwer et al. |
| 6,713,297 | B2 | 3/2004  | McMillan et al. |

FOREIGN PATENT DOCUMENTS

| EP |       | 1157744 A1    | 11/2001 |
| WO |       | WO 0194634 A2 * | 12/2001 |
| WO |       | WO-03/066897 A2 | 8/2003 |

OTHER PUBLICATIONS

Read et al. (2001) Journal of Clinical Microbiology vol. 39 No. 9 p. 3056-3059.*
Elnifro et al. (2000) Clinical Microbiol. Rev. vol. 13 No. 4 pp. 559-570.*
Haff (1994) Genome research vol. 3: 332-337.*
Boldt et al. (1997) British journal of Haematology vol. 99 pp. 968-973.*
van Elden et al. (2001) Journal of Clinical Microbiology vol. 39 No. 1 pp. 196-200.*
Amar et al., "Detection and genotyping by real-time PCR/RFLP analyses of *Giardia duodenalis* from human feces," Journal of Medical Microbiology, 2003, vol. 52, pp. 681-683.*
Zhou et al., "High-resolution DNA melting curve analysis to establish HLA genotyping identity," Tissue Antigens, 2004, vol. 64, pp. 156-164.*
Kjoller et al., Detection of arbuscular mycorrhizal fungi (Glomales) in roots by nested PCR and SSCP (Single Stranded Conformation Polymorphism), Plant and Soil, 2000, vol. 226, pp. 189-196.*
Stanley et al., "Multiplexed Tandem PCR: Gene Profiling From Small Amounts of RNA Using SYBR Green Detection", *Nucleic Acids Research*, 2005, vol. 33, No. 20.
Zazzi et al., "Simultaneous Amplification of Multiple HIV-1 DNA Sequences From Clinical Specimens by Using Nested-Primer Polymerase Chain Reaction", *AIDS Research & Human Retroviruses*, vol. 9, No. 4 (1993).
R. Avner et al., "Preimplantation Diagnosis of Cystic Fibrosis by Simultaneous Detection of the E1282X and ΔF508 Mutations", *Human Reproduction*, vol. 9, No. 9, pp. 1676-1680 (1994).
G. Scobie et al., "Identification of the Five Most Common Cystic Fibrosis Mutations in Single Cells Using a Rapid and Specific Differential Amplification System", *Molecular Human Reproduction*, vol. 2, No. 3, pp. 203-207 (1996).
T.J.C. Anderson et al., "Twelve Microsatellite Markers for Characterization of *Plasmodium falciparum* From Finger-Prick Blood Samples", *Parasitology* (1999), 119, 113-125.
C.F.L. Amar et al., "Detection and Genotyping by Real-Time PCR/RFLP Analyses of *Giardia duodenalis* From Human Faeces", *Journal of Medical Microbiology* (2003), 52, 681-683.
Stanley; A poster presentation "Multiplexed PCR.ppt" in Apr. 2005 at Hunter Cell Biology Meeting in Pokolbin, New South Wales, Australia.
Stanley; An oral presentantion "Stanley presentation.pdf" in May 2005 at a Discovery Science and Biotechnology meeting (May 4-6) in Melbourne, Victoria, Australia.

(Continued)

*Primary Examiner* — Young J Kim
(74) *Attorney, Agent, or Firm* — Miles and Stockbridge

(57) ABSTRACT

The invention relates to improved methods of amplifying and optionally quantifying and/or identifying a plurality of selected nucleic acid molecules from a pool of nucleic acid molecules. A first round of multiplex amplification used where the amplification reaction is allowed to proceed to a point prior to that at which significant competition between amplicons for reaction components has occurred. This is the followed by a second round of amplification that typically includes a fluorescent reporter to allow for each of the selected nucleic acid sequences to be quantified. The methods are useful for the amplification and quantification of nucleic acids from a variety of sources, such as gene expression products, whereby many such products may be amplified and quantified from very limited samples and from degraded archival samples.

33 Claims, 13 Drawing Sheets

(56) References Cited

OTHER PUBLICATIONS

Wittwer et al; "Real-Time Multiplex PCR Assays" in Dec. 2001 at Department of Pathology, University of Utah School of Medicine in Salt Lake City, Utah; pp. 1-13; cited in ISR dated Oct. 18, 2006 (PCT/AU2006/001265 Filed Aug. 31, 2006).

Bertolini et al., "Multiplex Nested Reverse Transcription-Polymerase Chain Reaction in a Single Tube for Sensitive and Simultaneous Detection of Four RNA Viruses and *Pseudomonas savastanoi* pv. *savastanoi* in Olive Trees," Phytopathology, (Mar. 1, 2003), vol. 93, No. 3, pp. 286-292 (XP-002458960).

Schwarzenbach, "A diagnostic tool for monitoring multidrug resistance expression in human tumor tissues," Analytical Biochemistry, (2002), vol. 308, pp. 26-33 (XP-002532427).

Amar et al., "Detection and genotyping by real-time PCR/RFLP analyses of *Giardia duodenalis* for human faeces," Journal of Medical Microbiology (2003), 52, pp. 681-683 (XP003009143).

Bellau-Pujol et al., "Development of three multiplex RT-PCR assays for the detection of 12 respiratory RNA viruses," Journal of Virological Methods, (2005), 126, pp. 53-63 (XP004852659).

Orimo et al., "Regulation of the human tissue-nonspecific alkaline phosphatase gene expression by all-trans-retinoic acid in SaOS-2 osteosarcoma cell line," Bone, (2005), 36, pp. 866-876 (XP004874709).

Grace et al., "Degradable dUMP Outer Primers in Merged Tandem (M/T)-Nested PCR: Low- and Single-Copy DNA Target Amplification," Analytical Biochemistry, (1998), 263, pp. 85-92 (XP-002152587).

Stanley et al., "Multiplexed tandem PCR: gene profiling from small amounts of RNA usin SYBR Green detection," Nucleic Acids Research, 2005, vol. 33, No. 20, pp. 1-9 (XP003009144).

Supplementary European Search Report, EP 06 77 4894, Jun. 16, 2009 (4 pages).

\* cited by examiner

*Bioanalyzser analysis of reaction products*

```
                              SEQUENCE LISTING

<160> NUMBER OF SEQ ID NOS: 119

<210> SEQ ID NO 1
<211> LENGTH: 18
<212> TYPE: DNA
<213> ORGANISM: Artificial
<220> FEATURE:
<223> OTHER INFORMATION: Oligonucleotide

<400> SEQUENCE: 1
gatgaatctg cagggagg                                                        18

<210> SEQ ID NO 2
<211> LENGTH: 20
<212> TYPE: DNA
<213> ORGANISM: Artificial
<220> FEATURE:
<223> OTHER INFORMATION: Oligonucleotide

<400> SEQUENCE: 2
tcggtggata tggtccttct                                                      20

<210> SEQ ID NO 3
<211> LENGTH: 21
<212> TYPE: DNA
<213> ORGANISM: Artificial
<220> FEATURE:
<223> OTHER INFORMATION: Oligonucleotide

<400> SEQUENCE: 3
tgctacacat ttcccagatg a                                                    21

<210> SEQ ID NO 4
<211> LENGTH: 20
<212> TYPE: DNA
<213> ORGANISM: Artificial
<220> FEATURE:
<223> OTHER INFORMATION: Oligonucleotide

<400> SEQUENCE: 4
gattcttggt tttggcagga                                                      20

<210> SEQ ID NO 5
<211> LENGTH: 20
<212> TYPE: DNA
<213> ORGANISM: Artificial
<220> FEATURE:
<223> OTHER INFORMATION: Oligonucleotide

<400> SEQUENCE: 5
gcggaggaga acaaacagat                                                      20

<210> SEQ ID NO 6
<211> LENGTH: 20
<212> TYPE: DNA
<213> ORGANISM: Artificial
<220> FEATURE:
<223> OTHER INFORMATION: Oligonucleotide

<400> SEQUENCE: 6
```
tgaggcggta gtaggacagg                                           20

<210> SEQ ID NO 7
<211> LENGTH: 20
<212> TYPE: DNA
<213> ORGANISM: Artificial
<220> FEATURE:
<223> OTHER INFORMATION: Oligonucleotide

<400> SEQUENCE: 7
tggcactgtt gtttcacaag                                           20

<210> SEQ ID NO 8
<211> LENGTH: 20
<212> TYPE: DNA
<213> ORGANISM: Artificial
<220> FEATURE:
<223> OTHER INFORMATION: Oligonucleotide

<400> SEQUENCE: 8
aggtaacggc tgagggaact                                           20

<210> SEQ ID NO 9
<211> LENGTH: 20
<212> TYPE: DNA
<213> ORGANISM: Artificial
<220> FEATURE:
<223> OTHER INFORMATION: Oligonucleotide

<400> SEQUENCE: 9
gagcaggcaa atgtgcaata                                           20

<210> SEQ ID NO 10
<211> LENGTH: 22
<212> TYPE: DNA
<213> ORGANISM: Artificial
<220> FEATURE:
<223> OTHER INFORMATION: Oligonucleotide

<400> SEQUENCE: 10
tttttgtgca ccaacagact tt                                        22

<210> SEQ ID NO 11
<211> LENGTH: 20
<212> TYPE: DNA
<213> ORGANISM: Artificial
<220> FEATURE:
<223> OTHER INFORMATION: Oligonucleotide

<400> SEQUENCE: 11
ggagcactaa gcgagcactg                                           20

<210> SEQ ID NO 12
<211> LENGTH: 18
<212> TYPE: DNA
<213> ORGANISM: Artificial
<220> FEATURE:
<223> OTHER INFORMATION: Oligonucleotide

<400> SEQUENCE: 12
cctcattcag ctcggaac                                             18

<210> SEQ ID NO 13
<211> LENGTH: 20
<212> TYPE: DNA
<213> ORGANISM: Artificial

```
<220> FEATURE:
<223> OTHER INFORMATION: Oligonucleotide

<400> SEQUENCE: 13
caagatccgc agacgtgtaa                                                20

<210> SEQ ID NO 14
<211> LENGTH: 18
<212> TYPE: DNA
<213> ORGANISM: Artificial
<220> FEATURE:
<223> OTHER INFORMATION: Oligonucleotide

<400> SEQUENCE: 14
ggaggctcct tcctcctg                                                  18

<210> SEQ ID NO 15
<211> LENGTH: 19
<212> TYPE: DNA
<213> ORGANISM: Artificial
<220> FEATURE:
<223> OTHER INFORMATION: Oligonucleotide

<400> SEQUENCE: 15
tgctccatga ggagacacc                                                 19

<210> SEQ ID NO 16
<211> LENGTH: 20
<212> TYPE: DNA
<213> ORGANISM: Artificial
<220> FEATURE:
<223> OTHER INFORMATION: Oligonucleotide

<400> SEQUENCE: 16
ctctgacctt ttgccaggag                                                20

<210> SEQ ID NO 17
<211> LENGTH: 20
<212> TYPE: DNA
<213> ORGANISM: Artificial
<220> FEATURE:
<223> OTHER INFORMATION: Oligonucleotide

<400> SEQUENCE: 17
gtcagtgggc agatgctgta                                                20

<210> SEQ ID NO 18
<211> LENGTH: 20
<212> TYPE: DNA
<213> ORGANISM: Artificial
<220> FEATURE:
<223> OTHER INFORMATION: Oligonucleotide

<400> SEQUENCE: 18
agcccttcca aaggaattgt                                                20

<210> SEQ ID NO 19
<211> LENGTH: 20
<212> TYPE: DNA
<213> ORGANISM: Artificial
<220> FEATURE:
<223> OTHER INFORMATION: Oligonucleotide

<400> SEQUENCE: 19
tgggcctggt acaagatcac                                                20
```

<210> SEQ ID NO 20
<211> LENGTH: 20
<212> TYPE: DNA
<213> ORGANISM: Artificial
<220> FEATURE:
<223> OTHER INFORMATION: Oligonucleotide

<400> SEQUENCE: 20
gcctccatgt tcaggttctc                                              20

<210> SEQ ID NO 21
<211> LENGTH: 20
<212> TYPE: DNA
<213> ORGANISM: Artificial
<220> FEATURE:
<223> OTHER INFORMATION: Oligonucleotide

<400> SEQUENCE: 21
gggaaattct catggtttgc                                              20

<210> SEQ ID NO 22
<211> LENGTH: 20
<212> TYPE: DNA
<213> ORGANISM: Artificial
<220> FEATURE:
<223> OTHER INFORMATION: Oligonucleotide

<400> SEQUENCE: 22
cgattttctc caaagcctca                                              20

<210> SEQ ID NO 23
<211> LENGTH: 20
<212> TYPE: DNA
<213> ORGANISM: Artificial
<220> FEATURE:
<223> OTHER INFORMATION: Oligonucleotide

<400> SEQUENCE: 23
ccccacctca gagagttttg                                              20

<210> SEQ ID NO 24
<211> LENGTH: 19
<212> TYPE: DNA
<213> ORGANISM: Artificial
<220> FEATURE:
<223> OTHER INFORMATION: Oligonucleotide

<400> SEQUENCE: 24
gggcgttttt gctacgttt                                               19

<210> SEQ ID NO 25
<211> LENGTH: 20
<212> TYPE: DNA
<213> ORGANISM: Artificial
<220> FEATURE:
<223> OTHER INFORMATION: Oligonucleotide

<400> SEQUENCE: 25
ggagcaaaag gaagggttct                                              20

<210> SEQ ID NO 26
<211> LENGTH: 20
<212> TYPE: DNA
<213> ORGANISM: Artificial
<220> FEATURE:
<223> OTHER INFORMATION: Oligonucleotide

```
<400> SEQUENCE: 26
tgcattgtca ctttcccaaa                                            20

<210> SEQ ID NO 27
<211> LENGTH: 20
<212> TYPE: DNA
<213> ORGANISM: Artificial
<220> FEATURE:
<223> OTHER INFORMATION: Oligonucleotide

<400> SEQUENCE: 27
tcctggaaag atggcagttt                                            20

<210> SEQ ID NO 28
<211> LENGTH: 20
<212> TYPE: DNA
<213> ORGANISM: Artificial
<220> FEATURE:
<223> OTHER INFORMATION: Oligonucleotide

<400> SEQUENCE: 28
tggcagaaat gtcaccgtag                                            20

<210> SEQ ID NO 29
<211> LENGTH: 20
<212> TYPE: DNA
<213> ORGANISM: Artificial
<220> FEATURE:
<223> OTHER INFORMATION: Oligonucleotide

<400> SEQUENCE: 29
ctcagcaaca aaccatggaa                                            20

<210> SEQ ID NO 30
<211> LENGTH: 22
<212> TYPE: DNA
<213> ORGANISM: Artificial
<220> FEATURE:
<223> OTHER INFORMATION: Oligonucleotide

<400> SEQUENCE: 30
tccacatatc caaatgagga ag                                         22

<210> SEQ ID NO 31
<211> LENGTH: 20
<212> TYPE: DNA
<213> ORGANISM: Artificial
<220> FEATURE:
<223> OTHER INFORMATION: Oligonucleotide

<400> SEQUENCE: 31
gcaagacgtg acagcaacat                                            20

<210> SEQ ID NO 32
<211> LENGTH: 20
<212> TYPE: DNA
<213> ORGANISM: Artificial
<220> FEATURE:
<223> OTHER INFORMATION: Oligonucleotide

<400> SEQUENCE: 32
ttccagcttt ttggtgatga                                            20

<210> SEQ ID NO 33
```

```
<211> LENGTH: 20
<212> TYPE: DNA
<213> ORGANISM: Artificial
<220> FEATURE:
<223> OTHER INFORMATION: Oligonucleotide

<400> SEQUENCE: 33
gcagactttg ctttccttgg                                          20

<210> SEQ ID NO 34
<211> LENGTH: 22
<212> TYPE: DNA
<213> ORGANISM: Artificial
<220> FEATURE:
<223> OTHER INFORMATION: Oligonucleotide

<400> SEQUENCE: 34
tttcaaatcc aacaaagtct gg                                       22

<210> SEQ ID NO 35
<211> LENGTH: 20
<212> TYPE: DNA
<213> ORGANISM: Artificial
<220> FEATURE:
<223> OTHER INFORMATION: Oligonucleotide

<400> SEQUENCE: 35
attcaagcca ggaagaagca                                          20

<210> SEQ ID NO 36
<211> LENGTH: 20
<212> TYPE: DNA
<213> ORGANISM: Artificial
<220> FEATURE:
<223> OTHER INFORMATION: Oligonucleotide

<400> SEQUENCE: 36
tcggatctgg tgttgaagaa                                          20

<210> SEQ ID NO 37
<211> LENGTH: 20
<212> TYPE: DNA
<213> ORGANISM: Artificial
<220> FEATURE:
<223> OTHER INFORMATION: Oligonucleotide

<400> SEQUENCE: 37
atcaaagccc ctcctgagac                                          20

<210> SEQ ID NO 38
<211> LENGTH: 20
<212> TYPE: DNA
<213> ORGANISM: Artificial
<220> FEATURE:
<223> OTHER INFORMATION: Oligonucleotide

<400> SEQUENCE: 38
tggtggtggt gacactatgg                                          20

<210> SEQ ID NO 39
<211> LENGTH: 20
<212> TYPE: DNA
<213> ORGANISM: Artificial
<220> FEATURE:
<223> OTHER INFORMATION: Oligonucleotide

<400> SEQUENCE: 39
```

-continued

| | |
|---|---|
| gcatgcccgt atttatggag | 20 |

<210> SEQ ID NO 40
<211> LENGTH: 20
<212> TYPE: DNA
<213> ORGANISM: Artificial
<220> FEATURE:
<223> OTHER INFORMATION: Oligonucleotide

<400> SEQUENCE: 40

| | |
|---|---|
| ttgggtgttt tgccaatgta | 20 |

<210> SEQ ID NO 41
<211> LENGTH: 20
<212> TYPE: DNA
<213> ORGANISM: Artificial
<220> FEATURE:
<223> OTHER INFORMATION: Oligonucleotide

<400> SEQUENCE: 41

| | |
|---|---|
| gggctttgga caccaattac | 20 |

<210> SEQ ID NO 42
<211> LENGTH: 20
<212> TYPE: DNA
<213> ORGANISM: Artificial
<220> FEATURE:
<223> OTHER INFORMATION: Oligonucleotide

<400> SEQUENCE: 42

| | |
|---|---|
| gcagatgctt cagggttcag | 20 |

<210> SEQ ID NO 43
<211> LENGTH: 20
<212> TYPE: DNA
<213> ORGANISM: Artificial
<220> FEATURE:
<223> OTHER INFORMATION: Oligonucleotide

<400> SEQUENCE: 43

| | |
|---|---|
| aggacagcag cagaatggat | 20 |

<210> SEQ ID NO 44
<211> LENGTH: 20
<212> TYPE: DNA
<213> ORGANISM: Artificial
<220> FEATURE:
<223> OTHER INFORMATION: Oligonucleotide

<400> SEQUENCE: 44

| | |
|---|---|
| ggaatgcaag ctcattgtga | 20 |

<210> SEQ ID NO 45
<211> LENGTH: 19
<212> TYPE: DNA
<213> ORGANISM: Artificial
<220> FEATURE:
<223> OTHER INFORMATION: Oligonucleotide

<400> SEQUENCE: 45

| | |
|---|---|
| ctcctgtgcg tgtctccat | 19 |

<210> SEQ ID NO 46
<211> LENGTH: 20
<212> TYPE: DNA

```
<213> ORGANISM: Artificial
<220> FEATURE:
<223> OTHER INFORMATION: Oligonucleotide

<400> SEQUENCE: 46
ggtccgctga aaggactctt                                               20

<210> SEQ ID NO 47
<211> LENGTH: 20
<212> TYPE: DNA
<213> ORGANISM: Artificial
<220> FEATURE:
<223> OTHER INFORMATION: Oligonucleotide

<400> SEQUENCE: 47
caggaaaaac tcgccaaact                                               20

<210> SEQ ID NO 48
<211> LENGTH: 21
<212> TYPE: DNA
<213> ORGANISM: Artificial
<220> FEATURE:
<223> OTHER INFORMATION: Oligonucleotide

<400> SEQUENCE: 48
tggatcactg ttccttggtt t                                             21

<210> SEQ ID NO 49
<211> LENGTH: 20
<212> TYPE: DNA
<213> ORGANISM: Artificial
<220> FEATURE:
<223> OTHER INFORMATION: Oligonucleotide

<400> SEQUENCE: 49
tccagagact tcagggtgct                                               20

<210> SEQ ID NO 50
<211> LENGTH: 20
<212> TYPE: DNA
<213> ORGANISM: Artificial
<220> FEATURE:
<223> OTHER INFORMATION: Oligonucleotide

<400> SEQUENCE: 50
cggtagtgga ggtggaagac                                               20

<210> SEQ ID NO 51
<211> LENGTH: 19
<212> TYPE: DNA
<213> ORGANISM: Artificial
<220> FEATURE:
<223> OTHER INFORMATION: Oligonucleotide

<400> SEQUENCE: 51
ggcggattgg aaatgaact                                                19

<210> SEQ ID NO 52
<211> LENGTH: 20
<212> TYPE: DNA
<213> ORGANISM: Artificial
<220> FEATURE:
<223> OTHER INFORMATION: Oligonucleotide

<400> SEQUENCE: 52
tcacctttag ctggcagacc                                               20
```

```
<210> SEQ ID NO 53
<211> LENGTH: 20
<212> TYPE: DNA
<213> ORGANISM: Artificial
<220> FEATURE:
<223> OTHER INFORMATION: Oligonucleotide

<400> SEQUENCE: 53
aagcaatggc tttggtctaa                                              20

<210> SEQ ID NO 54
<211> LENGTH: 20
<212> TYPE: DNA
<213> ORGANISM: Artificial
<220> FEATURE:
<223> OTHER INFORMATION: Oligonucleotide

<400> SEQUENCE: 54
cacggatctg aagggtgaaa                                              20

<210> SEQ ID NO 55
<211> LENGTH: 21
<212> TYPE: DNA
<213> ORGANISM: Artificial
<220> FEATURE:
<223> OTHER INFORMATION: Oligonucleotide

<400> SEQUENCE: 55
tcacatctgc aagtacgttc g                                            21

<210> SEQ ID NO 56
<211> LENGTH: 20
<212> TYPE: DNA
<213> ORGANISM: Artificial
<220> FEATURE:
<223> OTHER INFORMATION: Oligonucleotide

<400> SEQUENCE: 56
cctgcctctt ttccacagaa                                              20

<210> SEQ ID NO 57
<211> LENGTH: 20
<212> TYPE: DNA
<213> ORGANISM: Artificial
<220> FEATURE:
<223> OTHER INFORMATION: Oligonucleotide

<400> SEQUENCE: 57
tgccacatgg taaggcataa                                              20

<210> SEQ ID NO 58
<211> LENGTH: 20
<212> TYPE: DNA
<213> ORGANISM: Artificial
<220> FEATURE:
<223> OTHER INFORMATION: Oligonucleotide

<400> SEQUENCE: 58
gcgaggaact cacgaagaac                                              20

<210> SEQ ID NO 59
<211> LENGTH: 20
<212> TYPE: DNA
<213> ORGANISM: Artificial
<220> FEATURE:
```

<223> OTHER INFORMATION: Oligonucleotide

<400> SEQUENCE: 59
caggcacttg gggtcaaata                                              20

<210> SEQ ID NO 60
<211> LENGTH: 20
<212> TYPE: DNA
<213> ORGANISM: Artificial
<220> FEATURE:
<223> OTHER INFORMATION: Oligonucleotide

<400> SEQUENCE: 60
gggcttgcag agcatttatc                                              20

<210> SEQ ID NO 61
<211> LENGTH: 24
<212> TYPE: DNA
<213> ORGANISM: Artificial
<220> FEATURE:
<223> OTHER INFORMATION: Oligonucleotide

<400> SEQUENCE: 61
caacagttga tctggattca ctaa                                         24

<210> SEQ ID NO 62
<211> LENGTH: 20
<212> TYPE: DNA
<213> ORGANISM: Artificial
<220> FEATURE:
<223> OTHER INFORMATION: Oligonucleotide

<400> SEQUENCE: 62
cggatttcat cctggatagc                                              20

<210> SEQ ID NO 63
<211> LENGTH: 20
<212> TYPE: DNA
<213> ORGANISM: Artificial
<220> FEATURE:
<223> OTHER INFORMATION: Oligonucleotide

<400> SEQUENCE: 63
gtgccaaaga gcatgcaata                                              20

<210> SEQ ID NO 64
<211> LENGTH: 20
<212> TYPE: DNA
<213> ORGANISM: Artificial
<220> FEATURE:
<223> OTHER INFORMATION: Oligonucleotide

<400> SEQUENCE: 64
gagccaacag acgaaaaagc                                              20

<210> SEQ ID NO 65
<211> LENGTH: 20
<212> TYPE: DNA
<213> ORGANISM: Artificial
<220> FEATURE:
<223> OTHER INFORMATION: Oligonucleotide

<400> SEQUENCE: 65
acacttcgtg gggtcctttt                                              20

```
<210> SEQ ID NO 66
<211> LENGTH: 20
<212> TYPE: DNA
<213> ORGANISM: Artificial
<220> FEATURE:
<223> OTHER INFORMATION: Oligonucleotide

<400> SEQUENCE: 66
caatgtccat gatcccttt                                                  20

<210> SEQ ID NO 67
<211> LENGTH: 20
<212> TYPE: DNA
<213> ORGANISM: Artificial
<220> FEATURE:
<223> OTHER INFORMATION: Oligonucleotide

<400> SEQUENCE: 67
ctcagggcac aggaaaacat                                                 20

<210> SEQ ID NO 68
<211> LENGTH: 20
<212> TYPE: DNA
<213> ORGANISM: Artificial
<220> FEATURE:
<223> OTHER INFORMATION: Oligonucleotide

<400> SEQUENCE: 68
gcagcaagga gaagcagatg                                                 20

<210> SEQ ID NO 69
<211> LENGTH: 20
<212> TYPE: DNA
<213> ORGANISM: Artificial
<220> FEATURE:
<223> OTHER INFORMATION: Oligonucleotide

<400> SEQUENCE: 69
gcagatgctt cagggttcag                                                 20

<210> SEQ ID NO 70
<211> LENGTH: 20
<212> TYPE: DNA
<213> ORGANISM: Artificial
<220> FEATURE:
<223> OTHER INFORMATION: Oligonucleotide

<400> SEQUENCE: 70
gttttggtgg tgaggcaaat                                                 20

<210> SEQ ID NO 71
<211> LENGTH: 20
<212> TYPE: DNA
<213> ORGANISM: Artificial
<220> FEATURE:
<223> OTHER INFORMATION: Oligonucleotide

<400> SEQUENCE: 71
gtttctcctc aatccggtga                                                 20

<210> SEQ ID NO 72
<211> LENGTH: 20
<212> TYPE: DNA
<213> ORGANISM: Artificial
<220> FEATURE:
<223> OTHER INFORMATION: Oligonucleotide
```

<400> SEQUENCE: 72
tcatctgctg tggctgttct                                              20

<210> SEQ ID NO 73
<211> LENGTH: 20
<212> TYPE: DNA
<213> ORGANISM: Artificial
<220> FEATURE:
<223> OTHER INFORMATION: Oligonucleotide

<400> SEQUENCE: 73
acatgacccc agccctctac                                              20

<210> SEQ ID NO 74
<211> LENGTH: 20
<212> TYPE: DNA
<213> ORGANISM: Artificial
<220> FEATURE:
<223> OTHER INFORMATION: Oligonucleotide

<400> SEQUENCE: 74
agagagtctt ggcccttttcc                                             20

<210> SEQ ID NO 75
<211> LENGTH: 20
<212> TYPE: DNA
<213> ORGANISM: Artificial
<220> FEATURE:
<223> OTHER INFORMATION: Oligonucleotide

<400> SEQUENCE: 75
tggagatctt cgacatgctg                                              20

<210> SEQ ID NO 76
<211> LENGTH: 20
<212> TYPE: DNA
<213> ORGANISM: Artificial
<220> FEATURE:
<223> OTHER INFORMATION: Oligonucleotide

<400> SEQUENCE: 76
gccatcaggt ggatcaaagt                                              20

<210> SEQ ID NO 77
<211> LENGTH: 20
<212> TYPE: DNA
<213> ORGANISM: Artificial
<220> FEATURE:
<223> OTHER INFORMATION: Oligonucleotide

<400> SEQUENCE: 77
cttgcagcga tacagctcag                                              20

<210> SEQ ID NO 78
<211> LENGTH: 20
<212> TYPE: DNA
<213> ORGANISM: Artificial
<220> FEATURE:
<223> OTHER INFORMATION: Oligonucleotide

<400> SEQUENCE: 78
ggtcctggta gtgtgggtct                                              20

<210> SEQ ID NO 79
<211> LENGTH: 21

```
<212> TYPE: DNA
<213> ORGANISM: Artificial
<220> FEATURE:
<223> OTHER INFORMATION: Oligonucleotide

<400> SEQUENCE: 79
gctgatgatg ttaagggcag t                                      21

<210> SEQ ID NO 80
<211> LENGTH: 20
<212> TYPE: DNA
<213> ORGANISM: Artificial
<220> FEATURE:
<223> OTHER INFORMATION: Oligonucleotide

<400> SEQUENCE: 80
tcctctccaa aatgccagag                                        20

<210> SEQ ID NO 81
<211> LENGTH: 20
<212> TYPE: DNA
<213> ORGANISM: Artificial
<220> FEATURE:
<223> OTHER INFORMATION: Oligonucleotide

<400> SEQUENCE: 81
cagtcagagg cgctatgtgt                                        20

<210> SEQ ID NO 82
<211> LENGTH: 20
<212> TYPE: DNA
<213> ORGANISM: Artificial
<220> FEATURE:
<223> OTHER INFORMATION: Oligonucleotide

<400> SEQUENCE: 82
agcgtgtgtg actgtgaagg                                        20

<210> SEQ ID NO 83
<211> LENGTH: 20
<212> TYPE: DNA
<213> ORGANISM: Artificial
<220> FEATURE:
<223> OTHER INFORMATION: Oligonucleotide

<400> SEQUENCE: 83
ctcttctccg cctccttctt                                        20

<210> SEQ ID NO 84
<211> LENGTH: 20
<212> TYPE: DNA
<213> ORGANISM: Artificial
<220> FEATURE:
<223> OTHER INFORMATION: Oligonucleotide

<400> SEQUENCE: 84
ccatgtggac ctgtcactgt                                        20

<210> SEQ ID NO 85
<211> LENGTH: 20
<212> TYPE: DNA
<213> ORGANISM: Artificial
<220> FEATURE:
<223> OTHER INFORMATION: Oligonucleotide

<400> SEQUENCE: 85
```
aagatgtaga gcgggccttt                                              20

<210> SEQ ID NO 86
<211> LENGTH: 21
<212> TYPE: DNA
<213> ORGANISM: Artificial
<220> FEATURE:
<223> OTHER INFORMATION: Oligonucleotide

<400> SEQUENCE: 86
gaaggaaact ggggagtctt g                                            21

<210> SEQ ID NO 87
<211> LENGTH: 20
<212> TYPE: DNA
<213> ORGANISM: Artificial
<220> FEATURE:
<223> OTHER INFORMATION: Oligonucleotide

<400> SEQUENCE: 87
ccttattcgc tccgacaaga                                              20

<210> SEQ ID NO 88
<211> LENGTH: 20
<212> TYPE: DNA
<213> ORGANISM: Artificial
<220> FEATURE:
<223> OTHER INFORMATION: Oligonucleotide

<400> SEQUENCE: 88
aaggaggagc tgctgaaaca                                              20

<210> SEQ ID NO 89
<211> LENGTH: 20
<212> TYPE: DNA
<213> ORGANISM: Artificial
<220> FEATURE:
<223> OTHER INFORMATION: Oligonucleotide

<400> SEQUENCE: 89
gcatggcacg tgtcttctta                                              20

<210> SEQ ID NO 90
<211> LENGTH: 20
<212> TYPE: DNA
<213> ORGANISM: Artificial
<220> FEATURE:
<223> OTHER INFORMATION: Oligonucleotide

<400> SEQUENCE: 90
gagcggagaa agcatttgtt                                              20

<210> SEQ ID NO 91
<211> LENGTH: 20
<212> TYPE: DNA
<213> ORGANISM: Artificial
<220> FEATURE:
<223> OTHER INFORMATION: Oligonucleotide

<400> SEQUENCE: 91
cttcgagatg ttccgagagc                                              20

<210> SEQ ID NO 92
<211> LENGTH: 20
<212> TYPE: DNA
<213> ORGANISM: Artificial

```
<220> FEATURE:
<223> OTHER INFORMATION: Oligonucleotide

<400> SEQUENCE: 92
tctgagtcag gcccttctgt                                                20

<210> SEQ ID NO 93
<211> LENGTH: 20
<212> TYPE: DNA
<213> ORGANISM: Artificial
<220> FEATURE:
<223> OTHER INFORMATION: Oligonucleotide

<400> SEQUENCE: 93
cctaccctct caacgacagc                                                20

<210> SEQ ID NO 94
<211> LENGTH: 20
<212> TYPE: DNA
<213> ORGANISM: Artificial
<220> FEATURE:
<223> OTHER INFORMATION: Oligonucleotide

<400> SEQUENCE: 94
ctctgacctt ttgccaggag                                                20

<210> SEQ ID NO 95
<211> LENGTH: 21
<212> TYPE: DNA
<213> ORGANISM: Artificial
<220> FEATURE:
<223> OTHER INFORMATION: Oligonucleotide

<400> SEQUENCE: 95
tggtgtttgg tctaggatgg a                                              21

<210> SEQ ID NO 96
<211> LENGTH: 20
<212> TYPE: DNA
<213> ORGANISM: Artificial
<220> FEATURE:
<223> OTHER INFORMATION: Oligonucleotide

<400> SEQUENCE: 96
tgctggtctg caagtcagag                                                20

<210> SEQ ID NO 97
<211> LENGTH: 19
<212> TYPE: DNA
<213> ORGANISM: Artificial
<220> FEATURE:
<223> OTHER INFORMATION: Oligonucleotide

<400> SEQUENCE: 97
agcaaccgca gttgacaag                                                 19

<210> SEQ ID NO 98
<211> LENGTH: 21
<212> TYPE: DNA
<213> ORGANISM: Artificial
<220> FEATURE:
<223> OTHER INFORMATION: Oligonucleotide

<400> SEQUENCE: 98
ttggaagagc tacctggaca a                                              21
```

```
<210> SEQ ID NO 99
<211> LENGTH: 20
<212> TYPE: DNA
<213> ORGANISM: Artificial
<220> FEATURE:
<223> OTHER INFORMATION: Oligonucleotide

<400> SEQUENCE: 99
cttcgagaag gcatctgagc                                               20

<210> SEQ ID NO 100
<211> LENGTH: 20
<212> TYPE: DNA
<213> ORGANISM: Artificial
<220> FEATURE:
<223> OTHER INFORMATION: Oligonucleotide

<400> SEQUENCE: 100
ccctcaaaca gctccttcac                                               20

<210> SEQ ID NO 101
<211> LENGTH: 20
<212> TYPE: DNA
<213> ORGANISM: Artificial
<220> FEATURE:
<223> OTHER INFORMATION: Oligonucleotide

<400> SEQUENCE: 101 aaaggggtt ggataaggtt                                                20

<210> SEQ ID NO 102
<211> LENGTH: 20
<212> TYPE: DNA
<213> ORGANISM: Artificial
<220> FEATURE:
<223> OTHER INFORMATION: Oligonucleotide

<400> SEQUENCE: 102
tgtggtggaa caactgaaag                                               20

<210> SEQ ID NO 103
<211> LENGTH: 22
<212> TYPE: DNA
<213> ORGANISM: Artificial
<220> FEATURE:
<223> OTHER INFORMATION: Oligonucleotide

<400> SEQUENCE: 103
cagcaaagtg tgaaacatct gg                                            22

<210> SEQ ID NO 104
<211> LENGTH: 20
<212> TYPE: DNA
<213> ORGANISM: Artificial
<220> FEATURE:
<223> OTHER INFORMATION: Oligonucleotide

<400> SEQUENCE: 104
gagatcaagc ggaaacttgg                                               20

<210> SEQ ID NO 105
<211> LENGTH: 20
<212> TYPE: DNA
<213> ORGANISM: Artificial
<220> FEATURE:
<223> OTHER INFORMATION: Oligonucleotide
```

```
<400> SEQUENCE: 105
gaccagtcaa cagggacat                                              20

<210> SEQ ID NO 106
<211> LENGTH: 20
<212> TYPE: DNA
<213> ORGANISM: Artificial
<220> FEATURE:
<223> OTHER INFORMATION: Oligonucleotide

<400> SEQUENCE: 106 gtaccctgc cctctgagac                                              20

<210> SEQ ID NO 107
<211> LENGTH: 20
<212> TYPE: DNA
<213> ORGANISM: Artificial
<220> FEATURE:
<223> OTHER INFORMATION: Oligonucleotide

<400> SEQUENCE: 107
cgaacatctg gctggttcac                                             20

<210> SEQ ID NO 108
<211> LENGTH: 20
<212> TYPE: DNA
<213> ORGANISM: Artificial
<220> FEATURE:
<223> OTHER INFORMATION: Oligonucleotide

<400> SEQUENCE: 108
tcctcccagt gcctgaatac                                             20

<210> SEQ ID NO 109
<211> LENGTH: 20
<212> TYPE: DNA
<213> ORGANISM: Artificial
<220> FEATURE:
<223> OTHER INFORMATION: Oligonucleotide

<400> SEQUENCE: 109
gggttcagag gctgattgtg                                             20

<210> SEQ ID NO 110
<211> LENGTH: 20
<212> TYPE: DNA
<213> ORGANISM: Artificial
<220> FEATURE:
<223> OTHER INFORMATION: Oligonucleotide

<400> SEQUENCE: 110
attgcaaatt cctgccattc                                             20

<210> SEQ ID NO 111
<211> LENGTH: 20
<212> TYPE: DNA
<213> ORGANISM: Artificial
<220> FEATURE:
<223> OTHER INFORMATION: Oligonucleotide

<400> SEQUENCE: 111
cagcaagagc agcagaatca                                             20

<210> SEQ ID NO 112
```

```
<210> SEQ ID NO 112
<211> LENGTH: 20
<212> TYPE: DNA
<213> ORGANISM: Artificial
<220> FEATURE:
<223> OTHER INFORMATION: Oligonucleotide

<400> SEQUENCE: 112
gactctcagg gtcgaaaacg                                               20

<210> SEQ ID NO 113
<211> LENGTH: 20
<212> TYPE: DNA
<213> ORGANISM: Artificial
<220> FEATURE:
<223> OTHER INFORMATION: Oligonucleotide

<400> SEQUENCE: 113
ggattagggc ttcctcttgg                                               20

<210> SEQ ID NO 114
<211> LENGTH: 20
<212> TYPE: DNA
<213> ORGANISM: Artificial
<220> FEATURE:
<223> OTHER INFORMATION: Oligonucleotide

<400> SEQUENCE: 114
gacctgaagg tggagctgtc                                               20

<210> SEQ ID NO 115
<211> LENGTH: 20
<212> TYPE: DNA
<213> ORGANISM: Artificial
<220> FEATURE:
<223> OTHER INFORMATION: Oligonucleotide

<400> SEQUENCE: 115
actgtgagaa cacgggcaat                                               20

<210> SEQ ID NO 116
<211> LENGTH: 21
<212> TYPE: DNA
<213> ORGANISM: Artificial
<220> FEATURE:
<223> OTHER INFORMATION: Oligonucleotide

<400> SEQUENCE: 116
tcacatctgc aagtacgttc g                                             21

<210> SEQ ID NO 117
<211> LENGTH: 20
<212> TYPE: DNA
<213> ORGANISM: Artificial
<220> FEATURE:
<223> OTHER INFORMATION: Oligonucleotide

<400> SEQUENCE: 117
cacggatctg aagggtgaaa                                               20

<210> SEQ ID NO 118
<211> LENGTH: 20
<212> TYPE: DNA
<213> ORGANISM: Artificial
<220> FEATURE:
<223> OTHER INFORMATION: Oligonucleotide

<400> SEQUENCE: 118
```

```
tggttggcaa caaaagtgac                                                  20

<210> SEQ ID NO 119
<211> LENGTH: 20
<212> TYPE: DNA
<213> ORGANISM: Artificial
<220> FEATURE:
<223> OTHER INFORMATION: Oligonucleotide

<400> SEQUENCE: 119
acagctgcag aggtctcgat                                                  20
```

METHODS FOR THE AMPLIFICATION, QUANTITATION AND IDENTIFICATION OF NUCLEIC

CROSS-REFERENCE TO RELATED APPLICATIONS

This application claims the benefit of U.S. provisional patent application No. 60/713,636, filed Sep. 1, 2005. This applications also claims priority to Australian patent application no. 2005205791, filed Sep. 1, 2005, and Canadian patent application no. 2545613, filed Apr. 5, 2006. The contents of all these applications are hereby incorporated herein by reference.

TECHNICAL FIELD

The present invention relates to methods of nucleic acid amplification, identification, and quantification and in particular to improved methods of amplifying and quantifying or identifying a plurality of genes or gene expression products for diagnostic, forensic and research use. The invention also relates to the more accurate amplification, identification, and quantification of multiple nucleic acid sequences from small and degraded samples of nucleic acids.

In particular, the invention relates to the simultaneous amplification and quantification of a plurality of nucleic acid molecules and will be described hereinafter with reference to this application. However, it will be appreciated that the invention is not limited to this particular field of use.

BACKGROUND

Any discussion of the prior art throughout the specification should in no way be considered as an admission that such prior art is widely known or forms part of the common general knowledge in the field.

Known methods for analysing gene expression include the use of PCR or nested PCR to amplify a selected cDNA sequence, representing the expression product of a single gene from a pool of cDNA molecules representing many different genes. In a single-gene PCR reaction the gene expression products from a single gene are typically amplified using one pair of primers in a single round of PCR. In a typical nested PCR amplification reaction a single very rare sequence is amplified by two sequential PCR reactions, each consisting of 30-40 cycles using a single nested primer combination. Nested PCR is normally used to obtain a clone of a rare sequence and is not normally considered for the quantification of gene expression or identification of a gene. In order to quantify the level of gene expression using PCR, the amount of each PCR product of interest is typically estimated using conventional quantitative real-time PCR (qPCR) to measure the accumulation of PCR products in real time after each cycle of amplification. This typically utilises a detectible reporter such as an intercalating dye, minor groove binding dye or fluorogenic probe whereby the application of light excites the reporter to fluoresce and the resultant fluorescence is typically detected using a CCD camera or photomultiplier detection system, such as that disclosed in U.S. Pat. No. 6,713,297 which is hereby incorporated by reference. While single-gene analysis methods are now routine, difficulties arise when multiple gene expression products must be amplified within the same PCR reaction in a multiplex PCR. In a multiplex amplification reaction, each individual gene expression product must compete for reaction components during PCR, such that the products of highly expressed genes, which are present at a high copy number at the start of the PCR reaction, effectively prevent the amplification of low copy number gene products by sequestering vital reaction components. This results in a pool of amplified gene products that may represent only a small number of highly expressed genes. Analysis of these products is further complicated by the large variation that occurs between replicate experiments making the accurate quantification of gene expression very difficult. While optimisation of primers and reaction components can alleviate this problem to some degree, this typically involves extensive experimentation and becomes far more difficult as the number of genes to be analysed in a multiplex reaction is increased, whereby four genes would typically be the maximum number that could be reliably analysed in an extensively optimised system. Gene expression analysis typically requires that the amount of each gene expression be estimated, which is further complicated in a multiplex PCR.

Modern Approaches to Multiplex PCR

Modern approaches to this problem include the use of fluorogenic detection systems such as Taqman® probes to detect each gene expression product individually by binding to these and releasing a specific detectible fluorescence (Exner M. M., and Lewinski. M. A. (2002). Sensitivity of multiplex real-time PCR reactions, using the LightCycler and the ABI PRISM 7700 Sequence Detection System, is dependent on the concentration of the DNA polymerase (*Molecular and Cellular Probes. October* 2002;16(5):351-7). These probes and their uses are described in U.S. Pat. Nos. 5,210,015; 5,487,972; 5,804,375; 5,994,056; 5,538,848 and 6,030,787 and are hereby incorporated by reference. This requires a real time thermal cycling machine having multiple channels for detecting fluorescence at different wavelengths. In addition, Taqman® probes are expensive to purchase and may also limit the particular region of sequence that can be analysed due to specific sequence requirements for probe binding.

Other fluorogenic approaches include the use of generic detection systems such as SYBR-green dye, which fluoresces when intercalated with the amplified DNA from any gene expression product as disclosed in U.S. Pat. Nos. 5,436,134 and 5,658,751 which are hereby incorporated by reference. While SYBR-green is inexpensive to use and has excellent fluorogenic properties it is not normally appropriate for estimating the level of gene expression in a multiplex PCR as the source of the fluorescence, with regard to each gene product, cannot be reliably determined.

Irrespective of the use of fluorogenic probes or SYBR-green dye as the detection system, multiplex PCR still suffers from the same problem where gene expression products compete for reaction components, thereby hampering the accurate quantification of gene expression from multiple genes.

High Throughput Approach

An alternative approach to multiplex gene expression measurements includes the use of microarrays. Microarrays can be used to quantify the expression of thousands of genes simultaneously. However microarrays typically require extensive operator training, large amounts of sample RNA, and expensive equipment. In addition, while the number of genes that can be analysed is large, the resultant quantification of gene expression is far less accurate, often leading to false positives.

Thus there is a need for a simple and inexpensive method that is suitable for use in any setting where the accurate quantification of the expression of multiple genes is required or where the detection of specific nucleic acids is required or where the production of multiple nucleic acid products is required. The invention is particularly suited to the amplification and detection of nucleic acids from very small samples such as blood spots, laser dissection microscopy samples, single cells and samples containing partially fragmented nucleic acids such as those taken from aged samples and formalin-fixed paraffin-embedded (FFPE) sections. However, the methods of the invention are equally applicable to larger samples and also those of high quality. Examples of settings in which the invention could be useful include but are not limited to: diagnostics; prognostics; forensics; environmental and product testing and monitoring; biological weapons detection; research and the like.

It is therefore an object of the present invention to overcome or ameliorate at least one of the disadvantages of the prior art, or to provide a useful alternative.

SUMMARY OF THE INVENTION

The present invention relates to methods of nucleic acid amplification and quantification and in particular to improved methods of amplifying and quantifying or identifying a plurality of gene expression products for diagnostic, forensic and research use. The methods are particularly applicable to the quantification or identification of gene expression from many genes using a small amount of starting material and may also be used on degraded samples such as those obtained from archival or forensic material. The skilled addressee will understand that the methods of the invention are equally applicable to the amplification of nucleic acids from other sources such as genomic DNA or viral DNA. The present invention involves the use of a two round tandem amplification protocol including a first round multiplex amplification reaction, which amplifies a plurality of selected nucleic acid sequences followed by a plurality of second round amplification reactions each typically further amplifying one of the selected nucleic sequences.

According to a first aspect of the invention there is provided a method of amplifying a plurality of selected nucleic acid molecules from a pool of nucleic acid molecules comprising:
  (a) amplifying a plurality of selected nucleic acid molecules in a first round multiplex amplification reaction including a plurality of outer primer pairs each pair being specific for a selected nucleic acid sequence wherein the amplification reaction is allowed to proceed to a point prior to that at which significant competition between amplicons for reaction components has occurred; and
  (b) further amplifying the selected nucleic acid molecules in a plurality of second round amplification reactions, each including a portion of the completed multiplex reaction as a template and at least one pair of inner primers each pair being specific for one of the selected nucleic acid sequences such that each second round reaction further amplifies a subset of the plurality of selected nucleic acid molecules respectively.

According to a second aspect of the invention there is provided a method of amplifying a plurality of selected nucleic acid molecules from a pool of nucleic acid molecules comprising:
  (a) amplifying a plurality of selected nucleic acid molecules in a first round multiplex amplification reaction including a plurality of outer primer pairs each pair being specific for a selected nucleic acid sequence wherein the amplification reaction is allowed to proceed to a point prior to that at which significant competition between amplicons for reaction components has occurred; and
  (b) further amplifying the selected nucleic acid molecules in a plurality of second round amplification reactions, each including a portion of the completed multiplex reaction as a template and at least one pair of primers each pair comprising an inner primer and one of the outer primers and being specific for one of the selected nucleic acid sequences such that each second round reaction further amplifies a subset of the plurality of selected nucleic acid molecules respectively.

According to a third aspect of the invention there is provided a method of estimating the number of selected nucleic acid molecules from a pool of nucleic acid molecules comprising:
  (a) amplifying a plurality of selected nucleic acid molecules in a first round multiplex amplification reaction including a plurality of outer primer pairs each pair being specific for a selected nucleic acid sequence wherein the amplification reaction is allowed to proceed to a point prior to that at which significant competition between amplicons for reaction components has occurred;
  (b) further amplifying the selected nucleic acid molecules in a plurality of second round amplification reactions, each including a detectible reporter, a portion of the completed multiplex reaction as a template and at least one pair of inner primers each pair being specific for one of the selected nucleic acid sequences whereby each second round reaction further amplifies a subset of the plurality of selected nucleic acid molecules respectively; and
  (c) monitoring each second round amplification reaction by means of the detectible reporter such that the number of selected nucleic acid molecules of each selected sequence is estimated.

According to a fourth aspect of the invention there is provided a method of estimating the number of selected nucleic acid molecules from a pool of nucleic acid molecules comprising:
  (a) amplifying a plurality of selected nucleic acid molecules in a first round multiplex amplification reaction including a plurality of outer primer pairs each pair being specific for a selected nucleic acid sequence wherein the amplification reaction is allowed to proceed to a point prior to that at which significant competition between amplicons for reaction components has occurred; and
  (b) further amplifying the selected nucleic acid molecules in a plurality of second round amplification reactions, each including a detectible reporter, a portion of the completed multiplex reaction as a template and at least one pair of primers each pair comprising an inner primer and one of the outer primers and being specific for one of the selected nucleic acid sequences such that each second round reaction further amplifies a subset of the plurality of selected nucleic acid molecules respectively; and
  (c) monitoring each second round amplification reaction by means of the detectible reporter such that the number of selected nucleic acid molecules of each selected sequence is estimated.

In one embodiment of the invention, the fully nested form of the Multiplex Tandem-Polymerase Chain Reaction (MT-PCR) method is used according to the first and third aspects, whereby each selected nucleic acid molecule is amplified using a pair of outer primers in the first round of amplification and two inner primers in the second round of amplification.

In another embodiment of the invention, the hemi-nested MT-PCR method is used according to the second and fourth aspects, whereby each selected nucleic acid molecule is amplified using a pair of outer primers in the first round of amplification and the selected nucleic acid sequence is amplified further in the second round of amplification using a pair of primers comprising one of the outer primers used in the first round of amplification paired with one inner primer.

Preferably, the fluorogenic reporter is SYBR-green or SYTO-9 dye.

The skilled addressee will understand that other fluorogenic dyes are also contemplated.

In some embodiments, the fluorogenic reporter is a fluorogenic probe.

In some embodiments, the second round amplification reaction includes a plurality of primer pairs and a plurality of fluorescent probes such that a plurality of selected nucleic acid molecules of each selected sequence are amplified and quantified by means of the fluorescent probes each being specific for a selected nucleic acid sequence.

The skilled addressee will recognise that the second round amplification reactions may be carried out simultaneously or sequentially.

Preferably, the nucleic acid molecules include DNA molecules.

Preferably, the primers included in the second round amplification reaction have a higher Tm than at least one of the outer primers included in the first round amplification reaction, such that the oligonucleotide priming in the second round amplification reaction is substantially biased in favour of the primers having the higher Tm.

In some embodiments, at least one of the outer primers includes UTP nucleotides whereby the primer is amenable to digestion by a UNG enzyme and the outer primers are removed at the end of the first round of amplification by digestion with a UNG enzyme thereby substantially preventing contamination of the second round amplification reaction by the first round primers.

Preferably, the number of multiplex amplification cycles used is selected having regard to the amount of nucleic acid used at the start of the reaction in order to minimise the effects of any competition between amplicons for reaction components during amplification by amplifying these to a point prior to that at which significant competition between amplicons for reaction components has occurred whilst providing specific amplification of each selected nucleic acid sequence. For example, where about 50 ng to about 500 ng of nucleic acid is used, about 10 cycles of multiplex amplification is preferred. Where about 0.5 to about 50 ng of nucleic acid is used, about 15 cycles of multiplex amplification is preferred. Where about 0.01 to about 0.5 ng of nucleic acid is used, about 20 cycles of multiplex amplification is preferred. It will be clear to the skilled addressee from the teaching provided in the present specification that a larger number of multiplex amplification cycles can be used when lower amounts of nucleic acid are input.

Preferably, the first round multiplex amplification reaction is allowed to proceed for between about 1 and about 30 cycles. More preferably, the first round multiplex amplification reaction is allowed to proceed for between about 5 and about 25 cycles, still more preferably, the first round multiplex amplification reaction is allowed to proceed for between about 5 and about 20 cycles and most preferably the first round multiplex amplification reaction is allowed to proceed for between about 10 and about 20 cycles.

While a standard multiplex PCR reaction can typically be used to amplify, quantify and identify only a limited number of different sequences (such as 4 sequences), it has been surprisingly found that the methods of the invention can be used to amplify, quantify and/or identify in excess of 150 selected sequences. Preferably, the multiplex amplification reaction of the invention amplifies more than about 4 selected nucleic acid molecules. More preferably the multiplex amplification reaction amplifies between about 4 and 150 selected nucleic acid molecules. Still more preferably, the multiplex amplification reaction amplifies between about 10 and 150 selected nucleic acid molecules and most preferably the multiplex amplification reaction amplifies between about 20 and 100 selected nucleic acid molecules.

The skilled addressee will understand that the maximum number of selected nucleic acid molecules that may be effectively amplified in the first round multiplex amplification reaction for a given sample and group of primers must be determined in each case having regard to the level of amplification required and the accuracy of the resultant quantification in the second round of amplification.

Preferably, the methods are used in a method of detecting polymorphisms, mutations, insertions and deletions.

In one embodiment, fluorogenic probes are used in the second round of amplification in order to detect nucleic acid variants such as polymorphisms, mutations, SNPs, methylations (after bisulphite treatment), insertions and deletions.

In some embodiments, the methods are used in the diagnosis of diseases and disorders.

In some embodiments, the methods are used for the diagnosis of a neoplasm.

In some embodiments, the neoplasm is breast cancer.

In some embodiments, the neoplasm is colorectal cancer.

The skilled addressee will recognise that the methods of the invention will be useful in a diagnostic test for any diseases or disorders that may be detected by the amplification and/or quantification of any given nucleic acid sequence.

In some embodiments, the methods are used for the detection and identification of selected organisms.

In some embodiments, the organisms are detected and identified by high resolution melt analysis.

Preferably, the organisms are selected from the group of bacteria, viruses, fungi, mycoplasma, and parasites.

Preferably, the method includes high resolution melt curve analysis and the melting curve is preferably generated having a resolution in the range of about $0.05°$ C. to about $0.02°$ C. and still more preferably at a resolution of less than $0.02°$ C.

The skilled addressee will understand that the methods of the invention may be applied to any genetic material that may be amplified wherein this material may be derived from any organism.

Preferably, the amplification reactions are automatically processed in a thermal cycling apparatus.

Preferably the thermal cycling apparatus is a multi-well real time thermal cycling apparatus.

In some embodiments, the thermal cycling apparatus is a continuous flow PCR device.

In some embodiments, the thermal cycling apparatus is a rotary thermal cycling apparatus.

According to a fifth aspect of the invention there is provided a method of identifying and/or quantifying at least one selected nucleic acid sequence including the steps of:
 (i) mixing one or more selected nucleic acid sequences with one or more detectible reporters;
 (ii) generating a melting curve by measuring the signal generated by said one or more detectible reporters;
 (iii) identifying and/or quantifying said one or more selected nucleic acid sequences from said melting curve.

Preferably, the melting curve is generated having a resolution in the range of about of about $0.05°$ C. to about $0.02°$ C. and still more preferably at a resolution of less than $0.02°$ C.

DESCRIPTION OF THE PREFERRED EMBODIMENT

Figure 1:
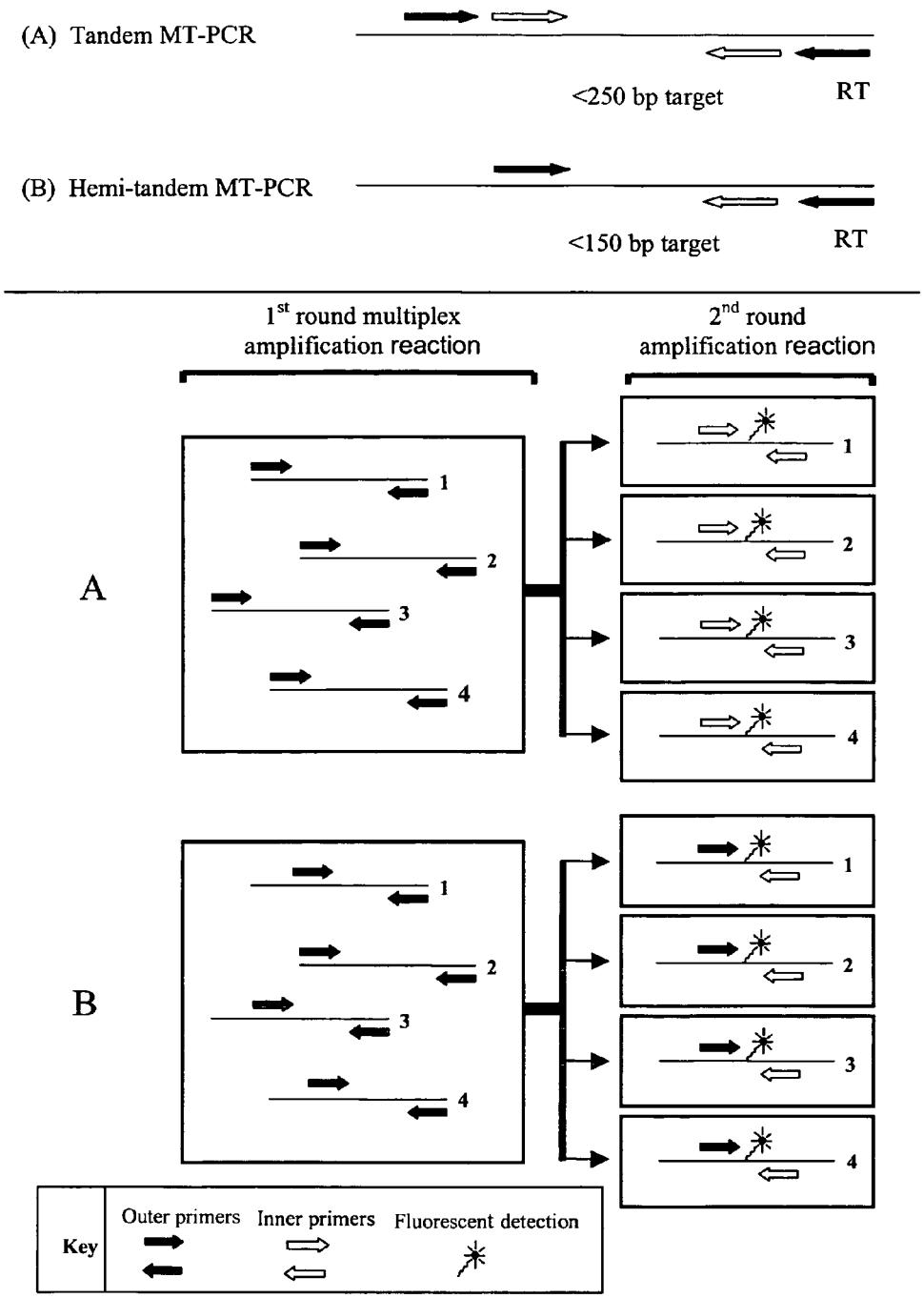
FIG. 1. Schematic diagram showing the arrangement of primers in MT-PCR illustrating both the tandem and hemi-tandem embodiments (A and B respectively), each shown in the process of amplifying and quantifying the gene expression products of 4 distinct genes (1-4).

A two round tandem PCR protocol called Multiplex Tandem Polymerase Chain Reaction (MT-PCR) was designed to accurately measure the expression of a large group of genes from a relatively small sample of nucleic acid in a reduced time at reduced cost. The problem inherent with multiplex PCR, whereby many gene expression products compete for reaction components, is overcome by the present invention whereby the multiplex amplification is limited to a preselected number of cycles such that competition between amplicons is minimised. Sensitivity is improved by using a two-round amplification, allowing all of the selected nucleic acid sequences, which are typically the expression products from a group of genes, to be measured using an amount of sample that would previously have been sufficient only to quantify products from a single selected sequence such as the expression products of a single gene. Overall processing time is reduced as the second round of nucleic acid amplification can use rapid cycling parameters.

In a preferred embodiment, costs are reduced by the use of SYBR-green DNA measurement rather than using costly, labeled oligonucleotide probes which were previously required in order to detect multiple sequences from multiplex reactions.

In another embodiment, fluorogenic probes such as Taqman® probes may also be used in order to detect and quantify the amplified products of single selected nucleic acid or a plurality of selected nucleic acids in the second round amplification reaction.

To analyse gene expression levels from clinical samples, RNA is first extracted from an appropriate tissue, typically from a biopsy sample preserved in formaldehyde, blood sample or other tissue. cDNA is then prepared from the RNA sample by reverse transcription, which may be done using random hexamers (for random priming) to prepare cDNA from the bulk of expressed sequences or more preferably by gene-specific methods.

In a preferred embodiment the reverse transcription reaction (RT reaction) is carried out using a multi-gene-specific priming method using each pair of outer primers specific to the selected nucleic acids of interest. These same outer primers are later used to amplify the specific gene expression products of interest in the first round multiplex amplification, the methods of which are hereinafter described. Using the same primers for reverse transcription and the first round of amplification reduces the number of oligonucleotides used in the reaction mix. Gene specific priming also reduced problems associated with RNA degradation allowing MT-PCR to be used with RNA extracted from formaldehyde-fixed paraffin-embedded (FFPE) specimens that have been stored for many years. The RT reaction is carried out for about one minute, which is sufficient to generate the required cDNA for later amplification. The multiplex amplification amplicons are typically of less than about 150 bp in length, which facilitates both efficient reverse transcription and later amplification. Improved results are also obtained using small amounts of RT enzyme in the reaction and in a preferred embodiment about 1 unit/µl of MMLV or superscript III enzyme is used in the RT reaction.

Reverse transcriptase is an inhibitor of PCR reactions and it is useful to remove or denature the enzyme prior to multiplex amplification. In a preferred embodiment, the reverse transcriptase is denatured prior to the multiplex amplification step by a heat step at about 95° C. This also serves to denature the cDNA to make it ready for the first round of multiplex amplification.

Preferably, a carrier protein is added to stabilise the enzymes in the first round reaction. Gelatin is satisfactory for this due to its low cost and stability at about 95° C., although BSA, crystalin and other proteins or stabilisers are suitable alternatives that may also be used.

The first round multiplex amplification typically contains the outer primers and components required to allow for the co-amplification of many expressed genes or sequence products in a multiplex amplification.

It will be evident to the skilled addressee, that the format of the reactions may be selected having regard to the equipment being used. For example, when using a "Gene-Disc" (Corbett Research, Sydney, Australia) which can be used to operate 72 amplification reactions, the expression products of about 24 genes may be quantified in triplicate using one such disk or 72 individual genes, or alternatively about 32 gene expression products may be quantified in triplicate using a 96-well plate format or the number may also be selected having regard to the statistical validity required.

The following described format relates to the use of a Corbett Research "Gene-Disc" although the skilled addressee will understand that for convenience, any other suitable format may be used such as a 384-well plate, 96-well plate, or continuous flow device.

Preferably, in each first round multiplex amplification, about 72 pairs of outer primers are used for amplifying about 72 sequences simultaneously, each representing the expression product of a gene or other expressed sequence.

Preferably, the outer primers are designed to amplify DNA fragments consisting of amplicons of approximately 250 bp of DNA or less from each gene expression products for fully-nested MT-PCR or about 150 bp or less for hemi-nested MT-PCR.

One skilled in the art, will recognise that the invention may also be applied to selected nucleic acid sequences of longer lengths using standard laboratory practice, wherein the alteration of conditions such as the length of time used in the RT reaction and the extension times used during the amplifications may also be increased in order achieve suitable cDNA synthesis and amplification.

To overcome the problem of competition between amplicons for reaction components during multiplex amplification, the amplification reaction is operated for a relatively low number of cycles, depending on the input level of RNA used. In an automated instrument the level of total DNA synthesis in the multiplex amplification reaction can be measured with an intercalating fluorogenic dye, such as SYBR-green dye, to ensure that this point is not exceeded. The number of cycles used in the first round multiplex amplification can be optimised having regard to the relative abundance of the selected nucleic acids and the sample size available such that, the amplification of these amplicons in the first round of multiplex amplification does not produce more than about 5% of the total amount of polynucleotides that would be produced in the reaction were the reaction allowed to proceed for a number of cycles beyond which point further amplification was no longer achieved. By this variant of the method, the pool of selected nucleic acid sequences (such as gene expression products) are prevented from amplifying to level where significant competition for reaction components occurs between their respective amplicons during multiplex amplification. Since the total amount of nucleic acid synthesised is still relatively small, there is always a large excess of reagents and therefore competition between the amplicons in the multiplex amplification reaction is substantially minimised.

The number of multiplex amplification cycles is selected according to the desired sensitivity of the detection reaction. Preferably, about 10 cycles of multiplex amplification are used for the detection of gene expression from a sample of about 50-500 ng of RNA. Preferably, about 15 cycles are used for the detection of gene expression from about 0.5 to 50 ng of RNA and preferably, about 20 cycles are used for detection from about 0.01 to 0.5 ng of RNA. The skilled addressee will recognise that a larger number of multiplex amplification cycles can be used when lower amounts of RNA are input.

In practice, where the same type and amount of sample are used, comparisons of gene expression are made between MT-PCR assays using the same number of multiplex amplification cycles.

In a preferred embodiment this first round of amplification is operated for 15 cycles with 10 ng of input RNA or DNA and a high level of nucleotide triphosphates (about 0.3 mM) is included in the reaction mix in order to further reduce the likelihood of competition between the amplicons. The concentration of outer primers in the first round multiplex amplification is also reduced to about 0.1 µM in order to further reduce the concentrations of these primers when the reaction products are transferred to the second round amplification reaction thereby reducing the effects of these primers on the second round amplification reaction.

While this reduces the significant problem of competition between amplicons in multiplex amplification, the amplification obtained using such a low number of amplification cycles does not provide sufficient amplification to allow for the accurate detection or quantification of the expressed nucleic acid sequences and the completed multiplex amplification reaction mix still contains a pool of amplified products derived from many expressed nucleic acid sequences. The further amplification of specific selected sequences from this pool in separate second round amplification reactions allows the amplification products from each gene or expressed sequence to amplify sufficiently for analysis on a substantially individual basis thereby accurately detecting and quantifying each selected nucleic acid sequence from an original pool of nucleic acids sequences.

The reduced amount of primers and Taq polymerase enzyme used in the second round of PCR further reduces the likelihood of non-specific product formation such as the formation of dimerised primers. In some embodiments about 0.5 units of Taq is used for each 20 µl second round amplification reaction and the primer concentration is reduced to about 0.2 µM. Preferably, about 2% DMSO is added to facilitate the amplification of GC rich amplicons under these conditions.

In a preferred embodiment about 35 cycles of second stage amplification is typically sufficient to allow for the accurate quantification of gene expression products from poorly expressed genes. It will be recognized by one skilled in the art that the number of cycles in the first and second rounds of amplification may also be varied to allow for the quantification of nucleic acids where these have been amplified from differing amounts of starting material prior to the first round multiplex amplification reactions, whereby the lower the amount of starting material used, the higher the number first and second round amplification cycles is typically required.

In one embodiment, an aliquot is taken from the completed first round multiplex amplification reaction and added to a number of independent tubes, each containing an individual second round amplification reaction mix. This aliquot may be diluted prior to addition into the second round reaction mixes or a small amount of first round products may be transferred such that a suitable level of dilution of the aliquot occurs at addition to the second round amplification reaction mixture.

Preferably, a 25× dilution of the first round multiplex amplification products is made prior to their addition to each second round reaction tube, wherein further dilution to a level of approximately 100× is obtained when the aliquot is diluted within the second round amplification reaction. One skilled in the art will recognise that the level of dilution may be varied, but that this should be typically be high enough to prevent the residual first round outer primers from effecting the accuracy of the quantification of each selected nucleic acid sequence in the second round of amplification.

This dilution step ensures that the amount of first round outer primers that pass from the first round multiplex amplification reaction into the second round of amplification is insignificant, such that further priming in the second round of amplification is substantially directed by the second round primers, thereby substantially amplifying only those selected molecules that are primed by the chosen second round primers.

Preferably, each individual second round amplification reaction includes a pair of inner primers, which have been selected to be complimentary to a subregion within one of the amplicons of one of the selected genes or expressed sequences amplified in the first round of multiplex amplification. Each pair of inner primers amplifies a shorter amplicon and in a preferred embodiment these shorter amplicons are about 70-90 bp or less.

In an alternative embodiment, an additional amount of one of the first round outer primers is added to the second round amplification reaction in combination with one of the corresponding inner primers in order to further amplify the selected nucleic acid sequence in a hemi-nested MT-PCR, where this amplicon is preferably of about 150 bp or less.

Thus by separating the amplification reaction for each gene or expressed sequence of interest in the second round of amplification, in which the bulk of amplification occurs, each amplicon is amplified free of competition from other sequences in an independent state which facilitates its further analysis.

In a preferred embodiment, processing time is reduced by the inclusion of the second round primers in a lyophilised form within the second round PCR reaction vessels. Examples of suitable reaction vessels include a "Gene-Disc" (Corbett Research), a 96 well PCR plate or a 384-well PCR plate (Applied Biosystems, USA). The first round amplification product/reaction component mix would then be added to the reaction vessels prior to the second round of amplification.

Preferably, the second round amplification reactions are also operated using fast cycling conditions to reduce the occurrence of false priming and reduce processing time.

Conveniently, in one embodiment of the invention, the first stage of multiplex amplification contains outer primers for about 36 genes based on the 72-well "Gene-Disc" format allowing each amplification to be run in duplicate using cDNA reverse transcribed from about 10 ng of total RNA. The first round amplification reactions contain outer primers, each at a concentration of about 0.1 μM in the presence of about 2% DMSO. At the end of the first round of about 10 amplification cycles, the reaction products are diluted about 25×, and about 5 μl of these diluted products are introduced into the second round of amplification. For the second round of amplification, fast cycling is used since the genes of interest have already been enriched in the template. Furthermore the inner primers are designed to bind within the selected amplicons produced from the multiplex amplification. These inner primers enable the amplification of short amplicons of about 70-90 bp so that short extension times are used in the second round of amplification. Typically the second round amplification cycling conditions are 1 s at 95° C., 10 s at 60° and 10 s at 72° C.

One skilled in the art will recognise that the number of sequences that may be co-amplified in the first round multiplex reaction may be varied as long as the inclusion of further pairs of first round outer primers does not lead to unwanted additional products in the second round of amplification, or affect the accuracy of quantification of the selected amplicons during the second round.

Because the reaction products introduced to the second round of amplification are enriched in the selected nucleic acid sequences of interest, the second stage can use fast cycling conditions and contain limiting concentrations of primers and enzyme which is conducive to the formation of unique and correct amplicon products in the second round of amplification. This results in the second round amplification products being substantially uncontaminated by non-specific DNA molecules or dimerised primers which would otherwise complicate or prevent analysis.

The reaction mixes used in the second round of amplification preferably include a detectable reporter component such as a fluorescent dye or fluorophore-containing probes such as Taqman® probes and one skilled in the art will recognize that specific annealing temperatures are required for the use of such probes.

In a preferred embodiment the reporter component is SYBR-green dye which fluoresces in response to the presence of amplified DNA in a non-specific manner, whereby the level of fluorescence is proportional to the amount of amplified DNA present in the second round amplification reaction. The second round amplification reactions are preferably monitored within a real-time PCR machine during amplification such that the development of this fluorescence is monitored and the amount of expressed sequences or gene products present in each reaction is quantified.

In an alternative embodiment, the second round amplification reaction may include primers for a plurality of selected nucleic acid sequences whereby detection and quantification of selected nucleic acid sequence is made using fluorogenic probes such as Taqman® probes or other suitably labeled oligonucleotide probes.

In a further embodiment, the methods of the invention are applied to the analysis of DNA to detect specific sequences associated with various traits (such as sought after traits and predispositions to diseases in mammals), SNPs, methylations (after bisulphite reaction), genetic disorders and the like.

The skilled addressee will recognise that the invention allows for the analysis of small samples such that this method is useful for but not limited to forensic analysis and the detection of parasitic, viral, fungal, bacterial, and mycoplasma, contamination of food, tissue, water, soil air and the like including bio-weapon detection.

In still a further embodiment, the processing of nucleic acids prior to PCR and the preparation of the PCR reactions is automated using suitable apparatus such as the CAS1200 robot (Corbett Research), the MultiPROBE® II Nucleic Acid Workstation (PerkinElmer Life and Analytical Sciences) and the epMotion™ 5075 Workstation (Eppendorf®) or other such apparatus as are well known in the art.

Preferably the nucleic acid amplification system is a PCR system, as described in U.S. Pat. Nos. 4,683,202, 4,683,195 and 4,965,188, which are hereby incorporated by reference.

Preferably the amplification, detection and quantification of the nucleic acids is achieved by the operation and monitoring of the reactions in an automated quantitative PCR thermal cycling apparatus, such as the Rotor Gene RG6000 (Corbett Research), Applied Biosystems 7900HT or other suitable instrument, examples of which are disclosed in EP1157744 and U.S. Pat. No. 6,713,297, which are hereby incorporated by reference.

Preferably the gene expression measurements are expressed relative to comparator genes run in the same batch of MT-PCR and only compared with gene expression measurements made under substantially similar conditions In other embodiments, the amplification reactions may be ligase chain reactions, self-sustaining sequence replication, rolling circle amplification, strand displacement amplification, isothermal DNA amplification and the like.

The skilled addressee will also recognise that the methods of the invention may be applied to any living cell or organism including, but not limited to: mammals (including humans); birds; fish; plants; reptiles; arthropods; gastropods; bacteria; viruses; fungi and mycoplasma.

The skilled addressee will also recognise that the methods of the invention may be used to detect the levels of selected nucleic acids from samples such as single mammalian cells from which approximately 0.01 ng of RNA is available and from a single FFPE tissue section, from which approximately 10 ng of RNA is obtained.

Preferably, the amplification reactions are automatically processed by a fluidics robot in a multi-well real time thermal cycler or continuous flow PCR device.

In another embodiment, the second round of amplification includes inner primers that anneal at a higher temperature (higher Tm) with respect to the outer primers, such that the annealing steps in the second round of amplification are operated at a higher temperature in order to specifically prime the second round of amplification using the inner primers thereby substantially preventing priming by the outer primers during the second round amplification reaction.

In a further embodiment, one or more UTP nucleotides are incorporated in one or more of the outer primers such that these primers are amenable to digestion by a UNG enzyme whereby the outer primers may be removed at the end of the first round of amplification thereby substantially preventing contamination of the second round amplification reactions by first round primers.

In another embodiment the methods are used in method of diagnosis such as in the diagnosis of neoplasms selected from a variety of solid tumours, both benign and malignant, as well as forms of leukaemia and the like.

The nucleic acid molecules described include RNA, DNA and cDNA molecules however it will be understood that related variants are also contemplated as long as they can be amplified.

Examples of fluorescent moieties that may be incorporated within oligonucleotide probes include but are not limited to the following examples: carboxy-X-rhodamine, fluorescein, 6-tetramethylrodamine-5(6)-carboxamide, BODIPY 493/503™, BODIPY-F1-X™, (4,6-Dichlorotriazinyl)aminofluorescein, 6-carboxyfluorescein, 6-((5-dimethylaminonaphthalene-1-sulfonyl)amino) hexanoate, Oregon Green 500™, Oregon Green 488™, Rhodol Green™, Oregon Green 514™, Rhodamine Green-X™, NBD-X, Tetrachlorofluorescein, 2',4',5',7'-Tetrabromosulfonefluorescein, BODIPY-F1 BR2™, BODIPY-R6G™, 6-Carboxy-4'-5'-dichloro-2',7'-dimethoxyfluorescein, BODIPY-530/550™, Hexachlorofluorescein, Carboxyrhodamine 6G™, BODIPY 558/568™, BODIPY-TMR-X™, 1-(3-carboxybenzyl)-4-(5-(4-methoxyphenyl)oxazol-2-yl)pyridinium bromide, BODIPY-564/570™, Cy3™, 6-(Tetramethylrhodamine-5(6)-carboxamido)hexanoate, Rhodamine Red-X™, BODIPY-576/589™, BODIPY-581/591™, Texas-Red-X™, Cy3.5™, BODIPY-TR-X™, Cy5™, carboxynaphthofluorescein, Cy5.5™.

Definitions

In the context of the present specification, the term "detectable reporter" refers to a component that provides a detectable means of measuring the amount of nucleic acid, this includes radio-labelled components, and fluorescent reporters such as dyes and probes (such as Taqman probes®) incorporating fluorescent moieties and the like.

In the context of the present specification, the term "fluorescent reporter" refers to a detectible reporter being either (1) an oligonucleotide sequence incorporating a nucleotide base, capable of fluorescence, which binds to a specific target DNA sequence and emits a specific detectible fluorescence in a manner that allows the amount of that nucleic acid to be quantified (also known as a probe or fluorogenic probe) or (2) a dye (such as SYBR-green dye), which binds to DNA to emit fluorescence in a manner that allows for detection, and/or quantification and/or identification of the sequence.

In the context of the present specification, the terms "probe" or "fluorogenic probe" refers to an oligonucleotide sequence incorporating a nucleotide base, capable of fluorescence, which binds to a specific target DNA sequence and emits a specific detectible fluorescence in a manner that allows the amount of that nucleic acid to be quantified. This also falls within the definitions of "detectable reporter" and "fluorescent reporter".

In the context of the present specification, the terms "polymerase chain reaction" and its acronym "PCR" are used according to their ordinary meaning as understood by those skilled in the art. Examples of PCR methods can be found in common molecular biology textbooks and reference manuals used in the art. For example PCR Technology: Principles and Applications for DNA Amplification (1989) Ed H A Erlich. Stockton Press, New York. An example of PCR is typically used to amplify a selected nucleic acid sequence using a heat-stable polymerase and a number of reagents and two short primers whereby the sequence to be amplified is "selected" by the inclusion of primers which bind to the sequence. One primer binds by complementary base pairing to the (+) strand at one end of the sequence to be amplified and the other primer other binds to the (−) strand at the other end. Because the newly synthesized DNA strands (amplicons) can subsequently serve as additional templates for the same primer sequences, successive rounds of primer annealing, strand elongation, and dissociation produce rapid and highly specific amplification of the selected sequence.

In the context of the present specification, the term "amplicon" refers to the newly synthesised DNA strands produced by a nucleic acid amplification process such as PCR.

In the context of the present specification, the terms "primer" and "oligonucleotide" refer to a short length of polynucleotide chain DNA used to start the amplification (copying) process in nucleic acid amplification (typically in a PCR reaction) or a reverse transcription reaction.

In the context of the present specification, the term "outer primer" refers to a primer that binds to a selected nucleic acid sequence or amplicon at a location that that is external to the region bound to by one or more corresponding inner primers as illustrated in FIG. 1. In the context of the present specification, the term "inner primer" refers to a primer that bind to an selected amplicon at a location that is internal to the binding location of the outer primers as illustrated in FIG. 1.

In the context of the present specification, the term "nested PCR" "fully-nested PCR" or "tandem PCR" refers to a nucleic acid amplification of two or more rounds (steps), which are typically comprised of two rounds of PCR, wherein the first round of PCR uses a pair of outer primers to amplify the selected nucleic acid molecule and the second round of amplification further amplifies the amplicons derived from the selected amplified nucleic acid molecule using a pair of inner primers that bind to the amplicon at a location that is internal to the binding location of the outer primers.

In the context of the present specification, the term "hemi-nested PCR" or "hemi-tandem PCR" refers to a form of PCR reaction wherein one of the first round outer primers is also included in the second round amplification reaction and primes the amplification of the selected amplicon in concert with a corresponding inner primer that binds to the same amplicon at a location internal to the binding location of the other first round outer primers.

In the context of the present specification, the terms "multiplex PCR" or "multiplex nucleic acid amplification" or "multiplex amplification" refer to a nucleic acid amplification reaction (typically PCR) that includes more than one pair of primers such that two or more different selected nucleic acid sequences are amplified by the reaction, in a single reaction vessel as illustrated in FIG. 1.

In the context of the present specification, the terms "selected nucleic acid molecule" and "selected nucleic acid sequence" refer to nucleic acid molecules of a specific nucleic acid sequence. For example, in the context of gene expression analysis, one selected nucleic acid sequence would refer to the gene expression products of a specific gene being of a specific nucleic acid sequence while a plurality of selected nucleic acid sequences would refer to the gene expression products of a plurality of specific genes.

In the context of the present specification, the term "nucleic acid" refers to a complex organic acid molecule composed of nucleotide subunits. The two main nucleic acids being DNA and RNA. This includes all subtypes of nucleic acid such as genomic DNA, mitochondrial DNA, chloroplast DNA, cDNA and the like. This also refers the various forms of RNA such as mRNA, tRNA, rRNA, viral RNA and the like.

In the context of the present specification, the term "cDNA" refers to a DNA sequence that was produced from mRNA by reverse transcription. A cDNA is so-called because its sequence is the complement of the original mRNA sequence.

In the context of the present specification, the term "mammal" includes humans, companion animals such as cats and dogs, and livestock animals such as horses, cattle, pigs, sheep and the like.

In the context of the present specification, the term "lyophilized" refers to a substance in a dry form, often crystallised or powdered.

In the context of the present specification, the term "organism" refers to any species of plant, animal, bacteria, fungi, virus, mycoplasma or genetically engineered organism and extends to parasitic DNA sequences and the like.

In the context of the present specification, the term "Tm", when applied to an oligonucleotide primer, refers to the temperature at which there is typically a 50% probability that the oligonucleotide would be bound in a duplex with its complimentary nucleic acid sequence.

In the context of the present specification, the term "UTP" refers to uridinetriphosphate.

In the context of the present specification, the term "Uracil N-glycosylase (UNG)" refers to an enzyme that is capable of hydrolysing the N-glycosidic bond between the deoxyribose sugar and uracil in DNA that contains deoxyuridine.

In the context of the present specification, the phrase "a point prior to that at which significant competition between amplicons for reaction components has occurred" refers to the cycle or stage within an amplification reaction past which further amplification of the selected nucleic acid sequences would be detrimental to the accuracy of the quantifications obtained in the second round of amplification. Without wishing to be bound by any particular mechanisms or theory, the detriment to the accuracy of the quantifications referred to, is considered to be due to competition between the amplifying sequences (amplicons) for reaction components such as dNTPs and primers. As the number of cycles is increased, these components become progressively more scarce, and thereby of a lower concentration in the reaction. As the available reaction components become more limited, this favours the amplification of the more abundant nucleic acid species, which interferes with the accuracy of quantification in the second round amplification reaction. The optimum number of cycles of multiplex amplification is therefore selected having regard to the amount of input nucleic acid in order to minimise the effects of any competition between amplicons for reaction components during amplification whilst providing specific amplification of each selected nucleic acid sequence. In practice, where for example 50-500 ng of nucleic acid is used, about 10 cycles of multiplex amplification is sufficient to amplify the selected nucleic acid molecules to a point prior to that at which significant competition between amplicons for reaction components has occurred. Similarly, where 0.5-50 ng of nucleic acid is used, about 15 cycles of multiplex amplification is preferred. Where 0.01-0.5 ng of nucleic acid is used, about 20 cycles of multiplex amplification is preferred. A larger number of multiplex amplification cycles can be used when lower amounts of nucleic acid are input. The number of multiplex amplification reaction cycles used in the methods of the invention typically do not result in the production of such large amounts of selected nucleic acid sequence products as to adversely affect the accuracy of their quantification as estimated in the second round of amplification.

The invention will now be described more particularly with reference to non-limiting examples.

EXAMPLES

Example 1

MT-PCR May be Used to Measure the Expression of Many Different Genes Using Multiplex Amplification from a Single Sample and Incorporating a SYBR-Green detection System in the Second Round of Amplification The multiplex amplification and measurement of multiple gene expression products using a generic reporter such as SYBR-green reporter dye is currently not possible. However, the MT-PCR method is capable of amplifying the expression products of many genes simultaneously. The MT-PCR method is outlined in FIG. 1 as a Schematic diagram showing the arrangement of primers in MT-PCR, illustrating both the tandem and hemi-tandem embodiments. The reverse outer primer, indicated as "RT", is typically used to prime the synthesis of cDNA, specific to each gene during the reverse transcription reaction prior to the amplification reactions illustrated. Both methods are shown in the process of amplifying and quantifying the gene expression products of 4 distinct genes (1-4), although in practice it is typical to amplify the expression products of 72 distinct genes. In tandem MT-PCR the outer primers are used as the multiplex primers while the inner primers are used in the second round amplification reactions when quantification of nucleic acid species is made. In hemi-tandem MT-PCR one of the inner primers is common between both the first round multiplex amplification reaction and the second round amplification reaction.

Figure 2A:
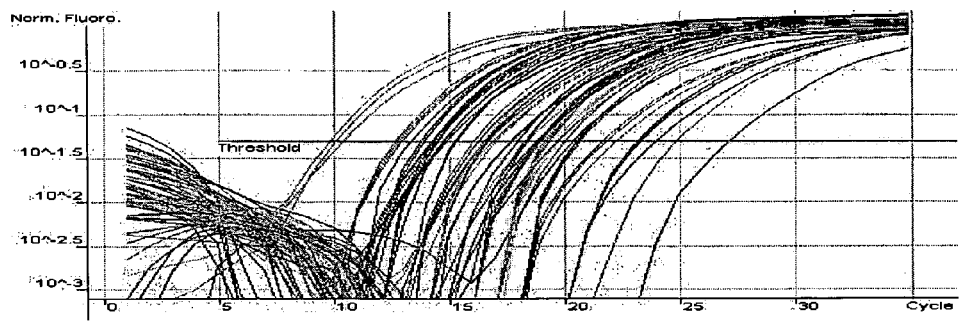
FIG. 2A. 24 of the triplicate gene expression measurements that were performed from a single RNA sample by hemi-tandem MT-PCR as measured in triplicate on a Corbett Research RG3000 using the primers in Tables 1 and 2, and the method described.
Figure 2B:
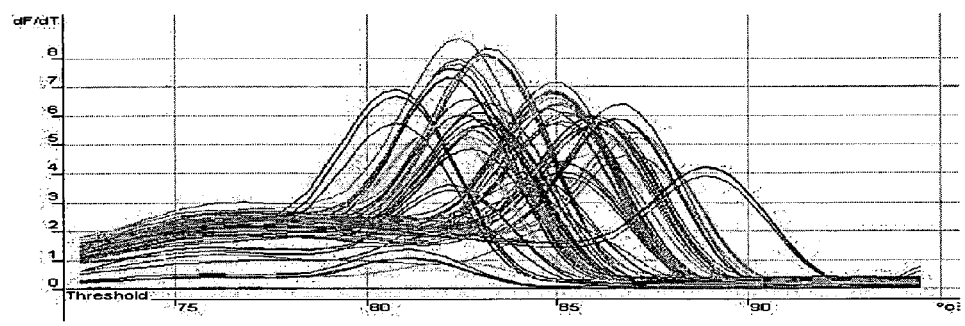
FIG. 2B. Melt curves relating to the 24 gene measurements shown in FIG. 2A.
Figure 2C:
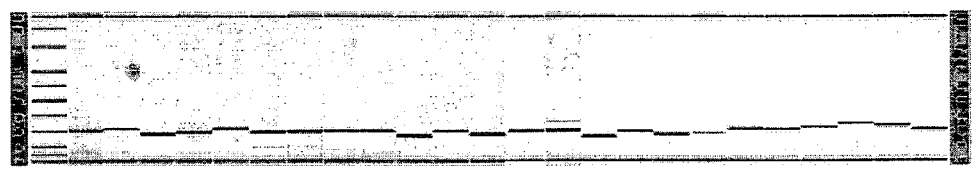
FIG. 2C. The products formed by MT-PCR for the 24 genes shown in FIG. 2A as analysed using a Bioanalyzer.

In order to demonstrate that the MT-PCR method is particularly effective in quantifying the expression products from multiple genes, 50 ng of RNA was extracted from MCF7 human epithelial cells and used in a hemi-tandem MT-PCR assay in a 72-well "gene disk" format to quantify the expression products from 72 distinct genes simultaneously using SYBR-green detection. In the first stage of the process, 72 oligonucleotide primer pairs, 24 of which are shown in Tables 1 and 2 were used. Each primer pair was specific for a given gene expression product, and these were added to 50 ng of RNA together with reverse transcriptase and Taq polymerase. After a 1 min reverse transcription reaction at 55° C. in which the reverse gene specific PCR primers act as primers for reverse transcription, the reverse transcriptase was denatured at 95° C. for 5 min and the 72 genes co-amplified for 10 cycles. Each cycle held the temperature at 95° C. for 5 s, 60° C. for 20 s and 72° C. for 20 s. The resultant product, now enriched in amplicons corresponding to the 72 genes was then divided into aliquots and each aliquot was further amplified and quantified in triplicate using one of the outer primers used in the multiplex amplification and a corresponding inner primer specific to that selected amplicon using the hemi-tandem MT-PCR method illustrated in FIG. 1. For this stage, cycles of 95° C. for 1 s, 60° C. for 10 s and 72° C. for 10 s were employed. Both stages of the assay were performed in an RG3000 Rotor-Gene Real Time Thermal Cycler (Corbett Research), which can combine any number of hold temperatures and cycling conditions. The result of the 72 amplification reactions, representing 24 gene expression measurements in triplicate, is illustrated in FIG. 2A. This result shows that each gene expression product was amplified in a reproducible manner, as each set of three lines corresponding to an individual gene measurement in triplicate have almost identical curves. Importantly, these products were also amplified with high specificity, as secondary amplification products were not detectable in these reactions as demonstrated by the corresponding melt curves shown in FIG. 2B, and the Bioanalyzer 'gel' image shown in FIG. 2C, which illustrates that each reaction yielded a single amplification product in each case.

TABLE 1

Hemi-tandem MT-PCR first round primers

| Gene | Forward | Reverse |
|---|---|---|
| ESR1 | GATGAATCTGCAGGGAGG | TCGGTGGATATGGTCCTTCT |
| TOP2A | TGCTACACATTTCCCAGATGA | GATTCTTGGTTTTGGCAGGA |
| CCND1 | GCGGAGGAGAACAAACAGAT | TGAGGCGGTAGTAGGACAGG |
| PTEN | TGGCACTGTTGTTTCACAAG | AGGTAACGGCTGAGGGAACT |
| MDM2 | GAGCAGGCAAATGTGCAATA | TTTTTGTGCACCAACAGACTTT |
| TP53 | GGAGCACTAAGCGAGCACTG | CCTCATTCAGCTCGGAAC |

TABLE 1-continued

Hemi-tandem MT-PCR first round primers

| Gene | Forward | Reverse |
|---|---|---|
| VEGF | CAAGATCCGCAGACGTGTAA | GGAGGCTCCTTCCTCCTG |
| MYC | TGCTCCATGAGGAGACACC | CTCTGACCTTTTGCCAGGAG |
| PgR | GTCAGTGGGCAGATGCTGTA | AGCCCTTCCAAAGGAATTGT |
| BSG | TGGGCCTGGTACAAGATCAC | GCCTCCATGTTCAGGTTCTC |
| GSTM3 | GGGAAATTCTCATGGTTTGC | CGATTTTCTCCAAAGCCTCA |
| MKI67 | CCCCACCTCAGAGAGTTTTG | GGGCGTTTTTGCTACGTTT |
| MELK | GGAGCAAAAGGAAGGGTTCT | TGCATTGTCACTTTCCCAAA |
| MAD2L1 | TCCTGGAAAGATGGCAGTTT | TGGCAGAAATGTCACCGTAG |
| BUB1 | CTCAGCAACAAACCATGGAA | TCCACATATCCAAATGAGGAAG |
| TPD52 | GCAAGACGTGACAGCAACAT | TTCCAGCTTTTTGGTGATGA |
| HPRT | GCAGACTTTGCTTTCCTTGG | TTTCAAATCCAACAAAGTCTGG |
| NAT1 | ATTCAAGCCAGGAAGAAGCA | TCGGATCTGGTGTTGAAGAA |
| E2F1 | ATCAAAGCCCCTCCTGAGAC | TGGTGGTGGTGACACTATGG |
| TGFB2 | GCATGCCCGTATTTATGGAG | TTGGGTGTTTTGCCAATGTA |
| TGFB3 | GGGCTTTGGACACCAATTAC | GCAGATGCTTCAGGGTTCAG |
| SMAD4 | AGGACAGCAGCAGAATGGAT | GGAATGCAAGCTCATTGTGA |
| RELA | CTCCTGTGCGTGTCTCCAT | GGTCCGCTGAAAGGACTCTT |
| BTF3 | CAGGAAAAACTCGCCAAACT | TGGATCACTGTTCCTTGGTTT |

TABLE 2

Hemi-tandem MT-PCR second round primers

| Gene | Forward | Reverse |
|---|---|---|
| ESR1 | GATGAATCTGCAGGGAGG | TCCAGAGACTTCAGGGTGCT |
| TOP2A | TGCTACACATTTCCCAGATGA | CGGTAGTGGAGGTGGAAGAC |
| CCND1 | GCGGAGGAGAACAAACAGAT | GGCGGATTGGAAATGAACT |
| PTEN | TGGCACTGTTGTTTCACAAG | TCACCTTTAGCTGGCAGACC |
| MDM2 | GAGCAGGCAAATGTGCAATA | AAGCAATGGCTTTGGTCTAA |
| TP53 | GGAGCACTAAGCGAGCACTG | CACGGATCTGAAGGGTGAAA |
| VEGF | CAAGATCCGCAGACGTGTAA | TCACATCTGCAAGTACGTTCG |
| MYC | TGCTCCATGAGGAGACACC | CCTGCCTCTTTTCCACAGAA |
| PgR | GTCAGTGGGCAGATGCTGTA | TGCCACATGGTAAGGCATAA |
| BSG | TGGGCCTGGTACAAGATCAC | GCGAGGAACTCACGAAGAAC |
| GSTM3 | GGGAAATTCTCATGGTTTGC | CAGGCACTTGGGGTCAAATA |
| MKI67 | CCCCACCTCAGAGAGTTTTG | GGGCTTGCAGAGCATTTATC |
| MELK | GGAGCAAAAGGAAGGGTTCT | CAACAGTTGATCTGGATTCACTAA |
| MAD2L1 | TCCTGGAAAGATGGCAGTTT | CGGATTTCATCCTGGATAGC |
| BUB1 | CTCAGCAACAAACCATGGAA | GTGCCAAAGAGCATGCAATA |

TABLE 2-continued

Hemi-tandem MT-PCR second round primers

| Gene | Forward | Reverse |
|---|---|---|
| TPD52 | GCAAGACGTGACAGCAACAT | GAGCCAACAGACGAAAAAGC |
| HPRT | GCAGACTTTGCTTTCCTTGG | ACACTTCGTGGGGTCCTTTT |
| NAT1 | ATTCAAGCCAGGAAGAAGCA | CAATGTCCATGATCCCCTTT |
| E2F1 | ATCAAAGCCCCTCCTGAGAC | CTCAGGGCACAGGAAAACAT |
| TGFB2 | GCATGCCCGTATTTATGGAG | GCAGCAAGGAGAAGCAGATG |
| TGFB3 | GGGCTTTGGACACCAATTAC | GCAGATGCTTCAGGGTTCAG |
| SMAD4 | AGGACAGCAGCAGAATGGAT | GTTTTGGTGGTGAGGCAAAT |
| RELA | CTCCTGTGCGTGTCTCCAT | GTTTCTCCTCAATCCGGTGA |
| BTF3 | CAGGAAAAACTCGCCAAACT | TCATCTGCTGTGGCTGTTCT |

Example 2

MT-PCR May be Used to Quantify Nucleic Acids, Such as Gene Expression Products, from Small Samples of Fragmented Nucleic Acids Such as Those Found in Archival FFPE Tissue Samples The quantification of gene expression from archival formalin-fixed paraffin-embedded (FFPE) samples is highly desirable, but limited by the low recovery of RNA from these specimens (about 10 ng per 10 µm section) and by the highly fragmented nature of the recovered molecules. It is not possible to perform linear RNA amplification or reverse transcription using oligo-dT primer as it is unlikely that any RNA fragment will contain both the 3' end of the RNA and the amplicon that is going to be measured. Thus current protocols only allow for the quantification of expression of a very small number of genes from each sample using gene specific or random primed reverse transcription.

Figure 3A:
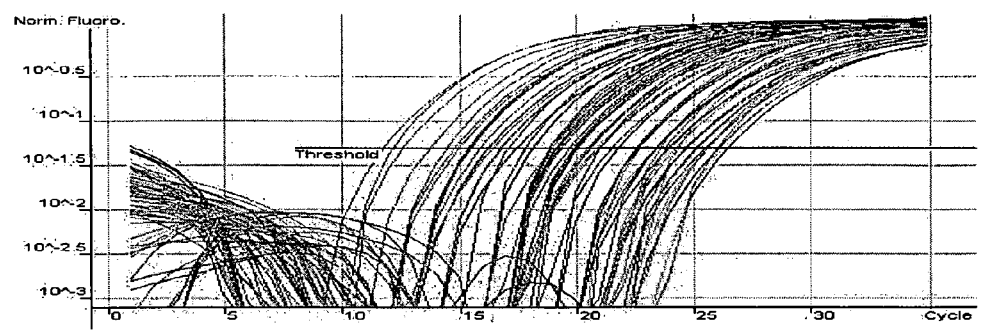
FIG. 3A. 24 gene expression product amplification curves (each in triplicate) using cDNA derived from a single section of FFPE material, having been amplified first using 15 cycles of multiplex PCR as a pool of 72 selected gene expression products where 24 of these were subsequently quantified in a second round of PCR.
Figure 3B:
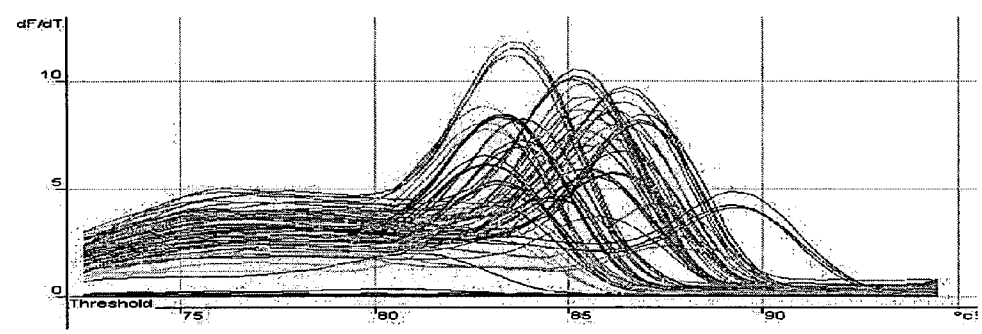
FIG. 3B. Melt curves for the 24 gene measurements shown in FIG. 3A.

In order to demonstrate that the MT-PCR method is particularly effective in amplifying many genes simultaneously from highly fragmented and degraded nucleic acid, RNA was first extracted from a single slice of a FFPE xenograft specimen that had been stored for 10 years prior to RNA extraction. The RNA was extracted from a section that was approximately 4 mm in diameter and 10 µm in thickness, using proteinase K digestion and silica column purification (Ambion). One third of the total RNA extracted from the FFPE slice, estimated to contain approximately 3 ng, was subsequently used in the hemi-tandem MT-PCR method as described in example 1 using the outer and inner primers shown in Tables 1 and 2 and where 15 cycles of multiplex amplification were used. The gene expression profiles from the 24 genes amplified in triplicate are illustrated in FIG. 3A. This shows that the method can be used to efficiently and reproducibly amplify and quantify gene expression products from very small amounts of fragmented RNA as demonstrated by the high reproducibility of the amplification curves. Importantly, these products were also amplified with high specificity as secondary amplification products were not detectable in these reactions as demonstrated by the corresponding melt curves shown in FIG. 3B, which illustrate that each reaction yielded a single amplification product represented by a single peak in each case. This result demonstrates that the method can be effectively used to amplify many different nucleic acid sequences from a very small amount of nucleic acid template, such as that obtained from single cells, laser dissected tissue biopsies, forensic samples and the like.

Example 3

Figure 4A:
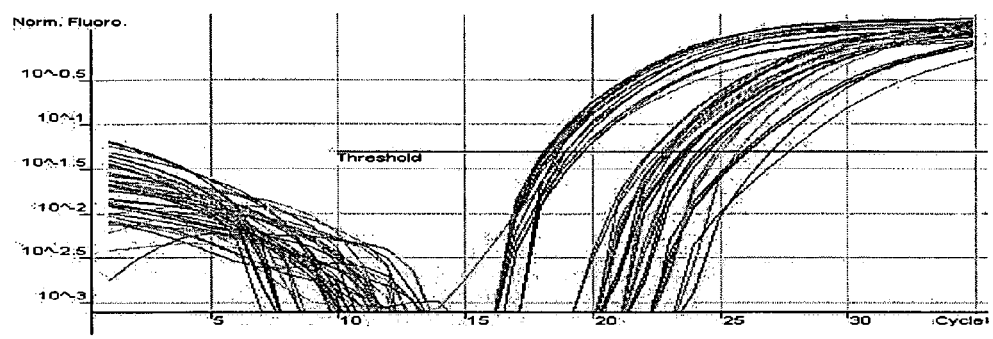
FIG. 4A. 24 gene expression product amplification curves (each in triplicate) from 10 pg of input RNA as shown in the second round of PCR following an initial 20 cycles of multiplex amplification.
Figure 4B:
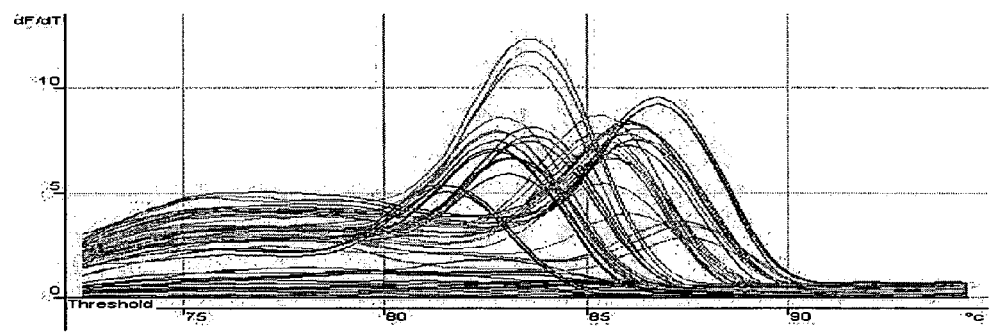
FIG. 4B. Melt curves for the 24 gene measurements shown in FIG. 4A

The Use of MT-PCR for the Amplification and Quantification of Nucleic Acids from Microsamples Obtained from Single Cells and Laser Dissections The MT-PCR method was used, which included 20 cycles of multiplex amplification in order to amplify and quantify the expression products of 24 genes using a sample of only 10 µg of RNA which is equivalent to the approximate amount of total RNA template that is typically obtained from a single mammalian cell. FIG. 4A shows the quantitation of 24 genes from 10 pg of MCF7 RNA and FIG. 4B shows the corresponding melt curves for each amplification product. 20 out of the 24 gene expression products were detected and quantified, without unwanted secondary amplification products. This result illustrates that the method can be effectively used to amplify many different nucleic acid sequences from a very small amount of nucleic acid template, such as that obtained from single cells, laser dissected tissue biopsies, forensic samples and the like. As indicated, it is necessary to use a relatively larger number of cycles in the multiplex amplification step in order to amplify the nucleic acids sufficiently from such a small amount of sample and 20 cycles was sufficient in this case. The method is particularly useful for forensic applications and the like where samples are frequently both very limited in size and where the nucleic acids are of a highly degraded/fragmented structure.

Example 4

Establishing Suitable Reaction Conditions and Parameters for MT-PCR

In order to establish an appropriate number of multiplex amplification cycles for a given multiplex reaction system, the appropriate cycle number must be empirically determined for a given sample/primer system. Ideally, the multiplex amplification step should be operated for a sufficient number of cycles in order to provide a sufficient level of amplification to facilitate the accurate quantification of each selected nucleic acid sequence in the second round of amplification. However, the number of multiplex amplification cycles must also be restricted such that this is not allowed to proceed for a number of cycles past which further amplification of the selected nucleic acid sequences would be detrimental to the accuracy of the quantifications obtained in the second round of amplification. The detriment to the accuracy of the quantifications referred to, is considered to be due to competition between the amplifying sequences (amplicons) for reaction components such as dNTPs and primers. As the number of cycles is increased, these components become progressively more scarce, and thereby of a lower concentration in the reaction.

Figure 5:
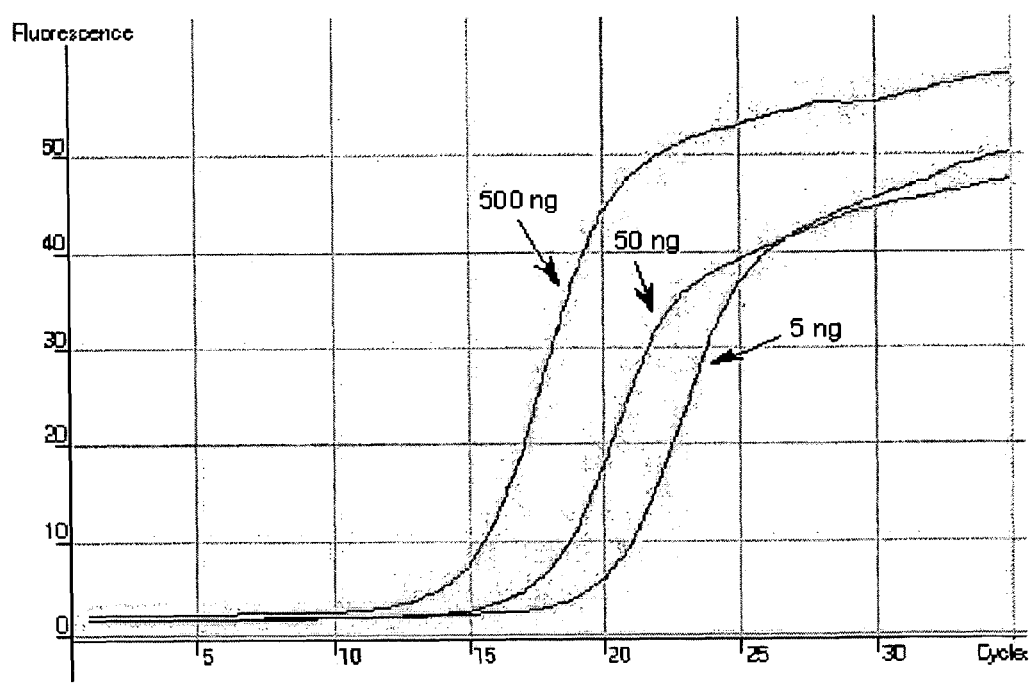
FIG. 5. Determination of a suitable number of multiplex amplification cycles in order to avoid competition between amplicons for reaction components during amplification. PCR of the most abundant gene used in the current gene set (BTF3) under the conditions of the multiplex PCR step. Amplification curves are illustrated where each amplification was started using cDNA derived from 5 ng, 50 ng and 500 ng of input RNA.

As a guide for establishing the appropriate number of cycles to use in a given first round multiplex amplification reaction, the exponential amplification of the most abundant mRNA species, or nucleic acid sequence, must not have significantly increased during the first round of amplification. The significant increase can be checked for using individual RT reactions each including a different amount of RNA input and then examining the amount of nucleic acid produced during the first round of amplification by the inclusion of SYBR-green dye to monitor the reaction. In this case the amplification reaction includes only the primers specific for one selected nucleic acid sequence, being the most abundant RNA species chosen, and this reaction is thereby not a multiplex amplification reaction, but is instead a uniplex reaction. As shown in FIG. 5, an input of 50-500 ng RNA produces only a small amount of nucleic acid from an abundant RNA species within the first 10 cycles of the reaction, showing that this is an appropriate number of cycles to use with this range of input RNA. As a general rule for establishing an appropriate number of multiplex amplification cycles to use, the multiplex amplification should be prevented from proceeding beyond a point at which more than 5% of the polynucleotides have been synthesised as a percentage of the total amount that is typically produced if the reaction is allowed to proceed for a sufficient number of cycles at which point further cycling no longer produces further amplification.

Thus, 10 cycles of multiplex PCR are recommended for routine research applications. This may be compared with conventional qPCR in which about 50 ng of RNA would normally be used to analyse the gene expression products of a single gene.

For inputs of 5-50 ng RNA, the first 15 cycles of the reaction produce only small amounts of nucleic acid for the most abundant RNAs as shown in FIG. 5, thus 15 cycles of multiplex PCR are recommended for samples of this scale, including the analysis of RNA samples from FFPE sections.

For inputs of 0.01-5 ng RNA, 20 cycles of multiplex amplification were possible before significant amplification of abundant RNA species had occurred as shown in FIG. 5. Thus 20 cycles of multiplex PCR is recommended for forensic, microbial and laser dissection microscopy samples. In practice, if 25 or more cycles of amplification are used to analyse very small amounts of sample in the multiplex amplification step, this higher cycle number favours the formation of primer dimers and secondary products, although the skilled addressee will recognise that using more than 25 cycles of multiplex PCR may be practical in some cases. Similar ranges of sensitivity would apply to the analysis of DNA as to RNA.

Figure 6A:
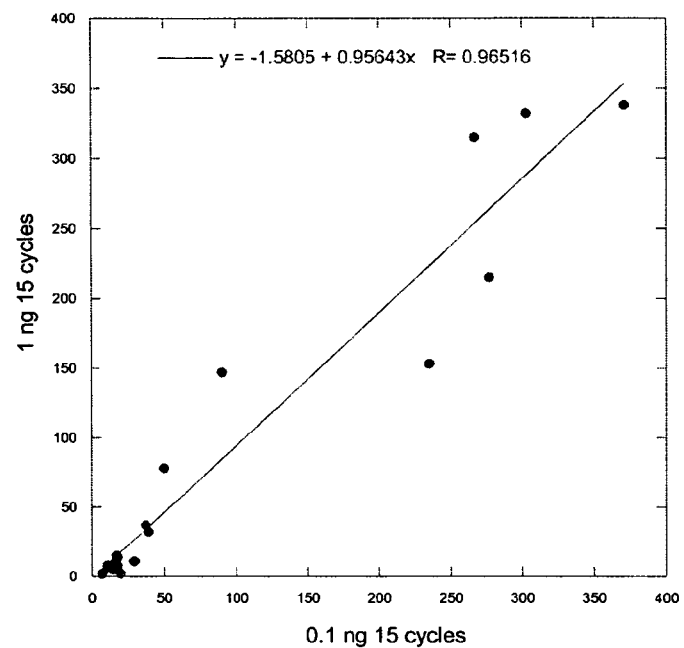
FIG. 6A. Quantification of gene expression relative to a comparator gene is maintained at different input RNA amounts.
Figure 6B:
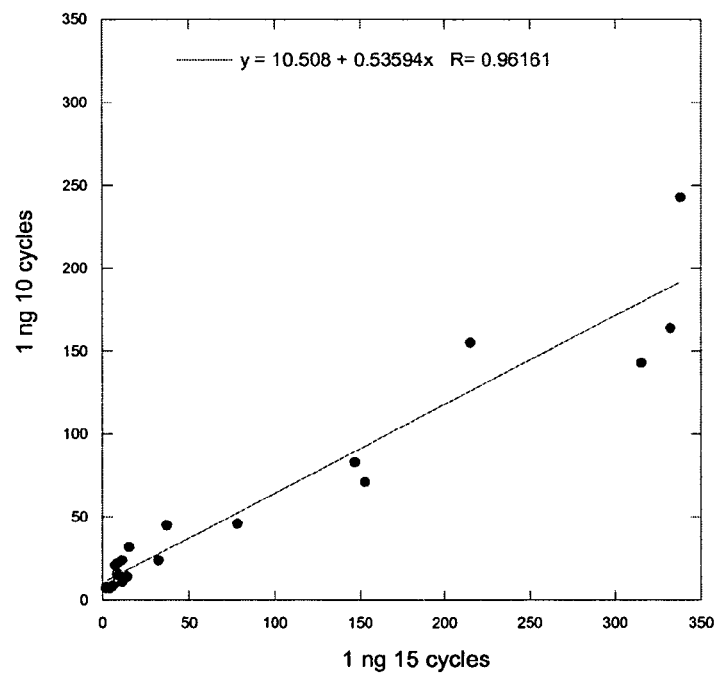
FIG. 6B. Varying the number of multiplex amplification cycles and the resultant effect on the quantification of gene expression.

In order to directly compare the accuracy of quantification when varying the amount of input RNA template or the number of multiplex amplification cycles, the gene expression products of 24 genes were amplified and quantified with these parameters varied. The resultant quantifications, made during 35 cycles of second round amplification, were compared when 0.1 ng or 1.0 ng of RNA were used (FIG. 6A) and where 10 or 15 cycles of multiplex amplification were used (FIG. 6B). In each case, the expression of 23 of the genes was quantified and compared as a ratio to a comparator gene in the same tandem MT-PCR assay in order to normalise the data. FIG. 6A illustrates that similar measurements were obtained when either 0.1 or 1 ng RNA were used, giving rise to a correlation coefficient of 0.96, demonstrating that fold changes in the amount of RNA used resulted in similar relative quantification values. When the same amount of RNA was measured using different numbers of multiplex amplification cycles, the correlation was still higher than 0.96, but a systematic error appears in the absolute fold differences as expected (FIG. 6B). This demonstrates that when quantifying the amount of nucleic acid such as the quantification of gene expression, each replicate experiment should be compared only where these employ the same number of multiplex amplification cycles.

Example 5

Figure 7A:
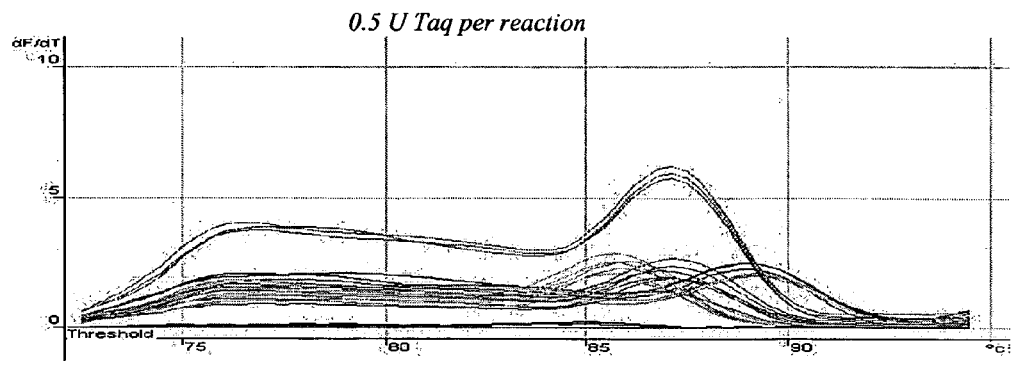
FIG. 7A. Melt curves obtained after the second round of amplification in order test the effects of using 0.5 units Taq per reaction in the second round amplification reaction of tandem MT-PCR.
Figure 7B:
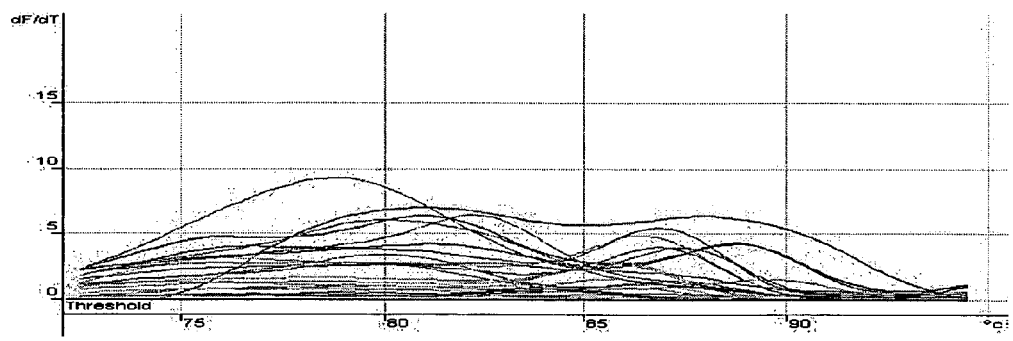
FIG. 7B. An identical experiment to that shown in FIG. 7A, where 1.0 units of Taq was used FIG. 7C. Melt curves obtained after the second round of amplification in order test the effects of using 20 units of reverse transcriptase for reverse transcription prior to the multiplex amplification step in tandem MT-PCR.

Establishing Suitable Taq Polymerase, Primer Concentrations and Reverse Transcriptase for Use in Tandem PCR in Order to Minimise the Formation of Primer Dimer In order to quantify the gene expression products from genes that are poorly expressed, a greater number of amplification cycles must typically be used in order to amplify the products sufficiently for analysis. In these cases it is common for primer dimers to form, which may complicate or preclude effective quantification by conventional methods. In order to minimise this problem using the methods of the present invention, the levels of Taq polymerase that should be included in the second round amplification reaction was optimised in an experiment to amplify and quantify the gene expression products of a group of rare genes (ERBB2, ESR1, TP53, MYC and GEM). Optimum performance was obtained when approximately 0.5 units Taq was incorporated in a 20 µl reaction with approximately 0.2 µM primers and 2% DMSO which resulted in clean melt curves as shown in FIG. 7A. A comparison between the use of 0.5 U or 1.0 U of Taq in the second round amplification reactions is illustrated by the resultant melt curves shown in FIGS. 7A and 7B respectively, which demonstrate that primer dimers can form when higher levels of Taq (such as 1.0 U) are used.

Figure 7C:
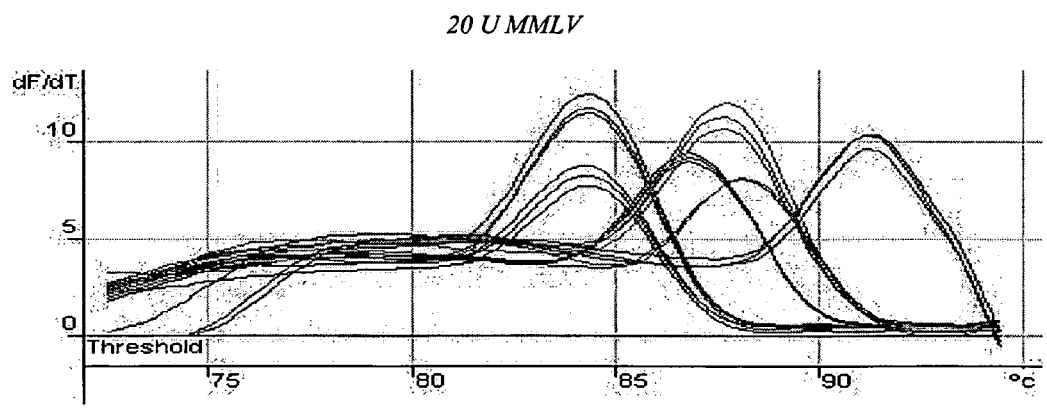
FIG. 7D. An identical experiment to that shown in FIG. 7C, where 200 units reverse transcriptase were used.
Figure 7D:
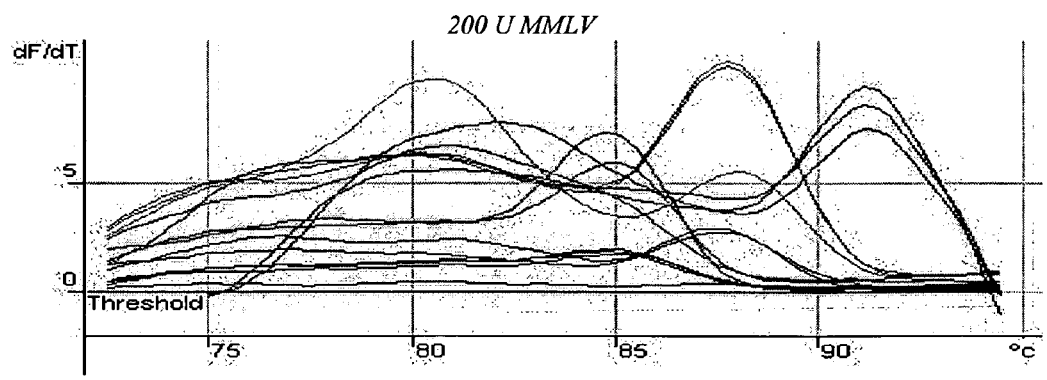

A similar experiment was then run where the amount of reverse transcriptase (MMLV) was varied during the synthesis of cDNA from the RNA template prior to subsequent amplification. The method was subsequently used to amplify a selection of highly expressed (TOP2A, BTF3, MDM2, RPL35), and poorly expressed genes (ESR1) and the effects of altered amounts of MMLV in the reverse transcription (RT) reaction on the quality of the later second round amplification reactions is illustrated by the resultant melt curves shown in FIGS. 7C and 7D. The melt curve in FIG. 7C shows that no significant secondary amplification products were obtained when approximately 20 U of MMLV had been used in the earlier RT reaction. However, when higher levels of approximately 200 U MMLV were used, this resulted in the later amplification of non-specific products as illustrated by the multiple peaks seen in the resultant melt curve shown in FIG. 7D. Similar results were also obtained using Superscript III reverse transcriptase (Invitrogen). Thus it is recommended that approximately 20 U of reverse transcriptase be used in a typical 20 µL RT reaction.

Example 6

Comparing the Reproducibility of Quantification Estimates Over Multiple Experiments Ten separate MT-PCR reactions were performed, on 4 different days from 50 ng of the same batch of RNA. Tandem MT-PCR was performed as described in example 1 using 10 cycles of multiplex PCR in the first round. Within a single run, the 20 µl RT mix was divided into 3×6 µl aliquots and used for 3 sets of 24 gene measurements which were then averaged to generate the data shown in Table 3. The means of these measurements were compared between the 10 runs. One gene (Nat1) was absent from the RNA and gave a flat cycling curve. The coefficient of variation in the Ct value varied from 0.01 to 0.05 with a mean value of 0.03 for all 23 detected genes demonstrating a particularly high level of precision between MT-PCR experiments.

TABLE 3

Comparison between the gene expression quantification estimates over multiple experiments.

| GENES | 1.0 | 2.0 | 3.0 | 4.0 | 5.0 | 6.0 | 7.0 | 8.0 | 9.0 | 10.0 | Mean | SD | CV |
|---|---|---|---|---|---|---|---|---|---|---|---|---|---|
| ESR1 | 28.1 | 28.1 | 28.2 | 28.0 | 28.0 | 27.8 | 27.7 | 27.5 | 27.7 | 27.6 | 27.9 | 0.24 | 0.01 |
| TOP2A | 19.8 | 20.7 | 21.5 | 20.9 | 21.5 | 20.1 | 20.4 | 20.1 | 19.7 | 19.7 | 20.4 | 0.69 | 0.03 |
| CCND1 | 18.5 | 19.6 | 19.8 | 18.9 | 18.5 | 17.7 | 16.9 | 17.7 | 18.2 | 18.1 | 18.4 | 0.88 | 0.05 |
| PTEN | 18.3 | 19.1 | 19.4 | 18.8 | 18.5 | 17.8 | 18.0 | 18.4 | 18.1 | 18.8 | 18.5 | 0.51 | 0.03 |
| MDM2 | 20.7 | 21.7 | 22.4 | 21.5 | 21.0 | 20.3 | 20.2 | 21.0 | 20.7 | 20.4 | 21.0 | 0.70 | 0.03 |
| TP53 | 19.8 | 20.0 | 20.4 | 20.0 | 19.1 | 18.1 | 18.1 | 19.3 | 19.1 | 19.0 | 19.3 | 0.78 | 0.04 |
| VEGF | 26.2 | 26.6 | 26.7 | 26.7 | 25.7 | 25.0 | 24.2 | 24.8 | 25.4 | 26.4 | 25.8 | 0.89 | 0.03 |
| MYC | 24.0 | 25.3 | 24.9 | 24.5 | 23.4 | 22.5 | 22.6 | 23.1 | 22.9 | 22.9 | 23.6 | 1.00 | 0.04 |
| PgR | 21.5 | 22.2 | 22.4 | 21.9 | 22.5 | 21.2 | 20.9 | 20.9 | 20.8 | 21.0 | 21.5 | 0.67 | 0.03 |
| BSG | 18.2 | 18.6 | 19.2 | 18.4 | 17.9 | 17.1 | 16.8 | 17.7 | 17.8 | 17.8 | 18.0 | 0.70 | 0.04 |
| GSTM3 | 20.3 | 21.1 | 22.0 | 21.6 | 20.7 | 19.7 | 20.5 | 19.8 | 19.6 | 19.9 | 20.5 | 0.83 | 0.04 |
| MKI67 | 17.3 | 18.3 | 18.4 | 17.8 | 17.9 | 17.4 | 16.6 | 17.3 | 17.4 | 17.5 | 17.6 | 0.53 | 0.03 |
| MELK | 21.1 | 22.3 | 23.1 | 22.5 | 22.1 | 21.3 | 21.6 | 21.3 | 21.2 | 21.4 | 21.8 | 0.67 | 0.03 |
| MAD2L1 | 24.2 | 24.5 | 24.7 | 24.2 | 23.9 | 23.0 | 23.2 | 23.2 | 23.1 | 22.6 | 23.7 | 0.72 | 0.03 |
| BUB1 | 25.4 | 26.2 | 26.4 | 26.7 | 26.0 | 25.2 | 24.7 | 24.7 | 25.0 | 24.9 | 25.5 | 0.74 | 0.03 |
| TPD52 | 23.4 | 24.6 | 24.4 | 24.3 | 23.5 | 23.0 | 22.8 | 22.7 | 22.7 | 23.0 | 23.4 | 0.74 | 0.03 |
| HPRT | 26.5 | 26.0 | 26.0 | 25.6 | 24.9 | 23.9 | 24.9 | 25.6 | 24.8 | 24.2 | 25.2 | 0.84 | 0.03 |
| NAT1 | 0.0 | 0.0 | 0.0 | 0.0 | 0.0 | 0.0 | 0.0 | 0.0 | 0.0 | 0.0 | 0.0 | 0.00 | |
| E2F1 | 20.1 | 21.2 | 20.6 | 20.5 | 19.7 | 19.0 | 18.2 | 19.4 | 19.3 | 19.4 | 19.7 | 0.88 | 0.04 |
| TGFB2 | 23.0 | 24.5 | 24.6 | 23.9 | 23.8 | 23.1 | 22.6 | 23.0 | 22.8 | 23.3 | 23.5 | 0.70 | 0.03 |
| TGFB3 | 25.3 | 26.7 | 26.1 | 26.3 | 24.9 | 23.6 | 22.4 | 24.3 | 24.5 | 24.2 | 24.8 | 1.32 | 0.05 |
| SMAD4 | 23.6 | 24.7 | 24.4 | 24.1 | 23.6 | 23.0 | 22.5 | 23.3 | 23.4 | 23.3 | 23.6 | 0.66 | 0.03 |
| NFkB | 25.0 | 26.8 | 25.9 | 26.1 | 24.1 | 23.2 | 23.1 | 23.7 | 24.3 | 23.8 | 24.6 | 1.29 | 0.05 |
| BTF3 | 14.2 | 14.9 | 14.9 | 14.6 | 14.6 | 14.1 | 13.6 | 14.0 | 14.2 | 14.1 | 14.3 | 0.42 | 0.03 |
| Mean | | | | | | | | | | | | | 0.03 |

Example 7

The Use of MT-PCR in the Quantification of Cancer-Related Gene Expression in Diagnosis Using a Cell Line Model 7.1 Measurement of Gene Expression in Tumour Derived Cell Line Tumour derived human breast cancer cell lines are believed to preserve much of the genetic makeup and physiological properties of the tumour cells from which they were derived. In this study we have measured the expression level of 24 genes in triplicate by hemi-nested MT-PCR in 15 human breast cancer cell lines.

7.2 Materials

An outer primer mix was made by mixing 2 μl of each of the 24 pairs of primers listed in Table 4 at 100 μM concentration together with 4 μl of water.

Preparation of Corbett Research "Gene-Disc" with Lyophilised Primers

Gene specific primer mixes, each containing a pair of primers as shown in Table 5, were prepared containing 10 μl of forward primer stock solution at 100 μM, 10 μl of corresponding reverse primer stock solution at 100 μM and 605 μl of water in a 0.2 ml tube. The CAS 1200 Robot (Corbett Research) was then used to aliquot 5 μl of each primer mix in triplicate into a Corbett Research gene disk. These aliquots were then lyophilised in the gene disk for 15 min with heating using a SpeedVac lyophiliser followed by sealing of the disk at 160° C. using the gene disk heat sealer. Each disk was then stored at 4° C. before use.

RT-PCR and PCR Stock Solutions

Gelatin—RNAse Free (5 ml)

50 mg of gelatin (Sigma G-2625) was added to 5.0 ml water and 5 μl DEPC followed by incubation at 60° C. for 1 h with occasional mixing and storage at −20° C. before use.

10× RT Buffer (10 ml)

500 mM TrisHCl (pH 8.5) containing 30 mM MgCl2, 300 mM KCl, 1 mM DTT and 0.1 mg/ml gelatin. This was stored at 20° C. in 0.5 ml aliquots before use.

10× PCR Buffer (10 ml)

200 mM TrisHCl (pH 8.5) containing 500 mM KCl, 30 mM MgSO4, and 1 μg/ml gelatin. This was stored at 20° C. in 0.5 ml aliquots before use.

7.3 Method

In brief, RNA was extracted from cultures of each cell line using the RNeasy method (Qiagen) and diluted so that 50 ng was used in each MT-PCR reaction. RT-PCR reaction mixes were prepared in a 0.2 ml thin walled PCR tube including: 50 ng of total RNA, outer primer mix to a final concentration of 0.1 μM of each primer, 0.3 mM dNTPs (Roche), RT-PCR buffer, DMSO to 2%, 0.5 μl RNAsin, 20 units MMLV (Invitrogen), 1 unit Taq DNA polymerase (Invitrogen).

First Round Multiplex Amplification

Each tube was placed in an RG3000 (Corbett Research) and heat treated as follows: 1 min at 55° C. (reverse transcription), 5 min at 95° C. (RT denaturation) followed by 10 cycles of: 10 s at 95° C., 20 s lat 60° C., 20 s at 72° C. This completed the multiplex PCR step and the product was diluted 1:50 in water.

Second Round Amplification Reaction Mix.

500 μl of the multiplex amplification products was added to each 1.5 ml of PCR reaction mix to give a final concentration of: 0.2 mM dNTPs, 2% DMSO, 25 U/ml Taq, PCR buffer, SYBR-green 1:20,000 dilution. 20 μl of PCR reaction mix was then added to each position within the gene disk (containing the lyophilised inner primers) and PCR was performed for 35 cycles of: is at 95° C., 10 s at 60° C. and 10 s at 72° C. Fluorescence was measured at the end of the 72° C. extension step. It should be noted that this protocol has also been successfully applied using both tandem and hemi-tandem MT-PCR.

7.4 Result

Figure 8:
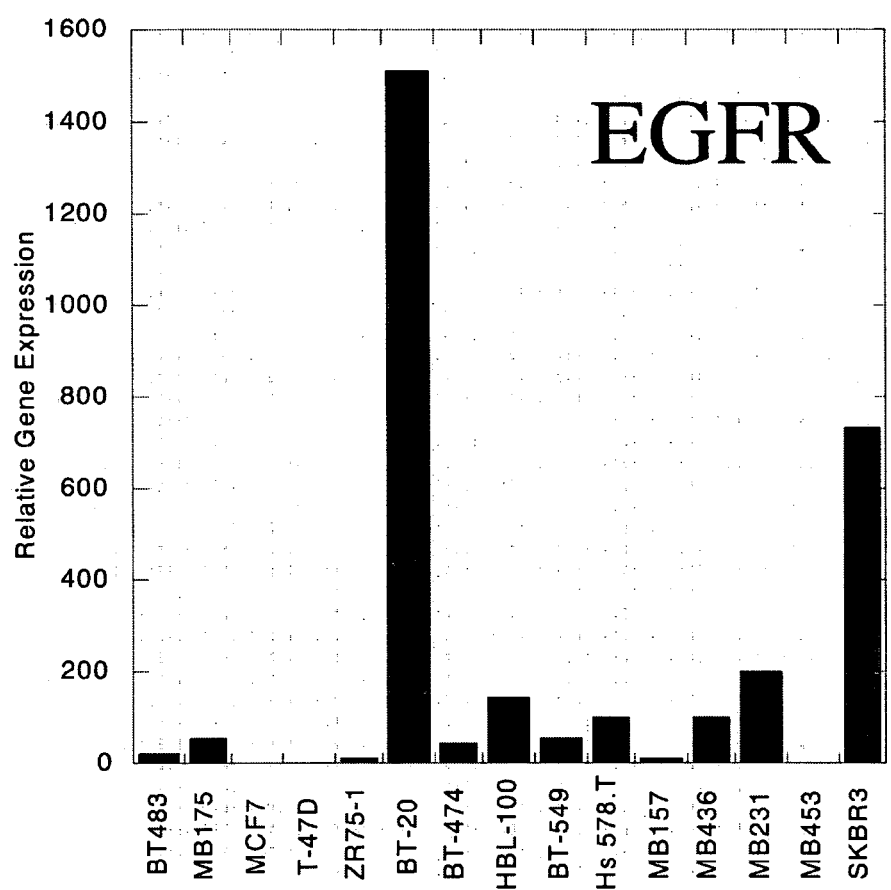
FIG. 8. Further diagnostic potential of MT-PCR: The expression of the EGFR gene in 15 cell lines of which BT20 and SKBR3 are known to over-express EGFR.

The expression of the epidermal growth factor receptor gene (EGFR) in each cell line was quantified using tandem MT-PCR. The data obtained from each cell line was normalised by use of an internal comparator gene to provide a relative quantification of EGFR expression in each of the 15 cell lines and these were then compared side-by-side as shown in FIG. 8. It can be seen that EGFR is highly expressed in only 2 of the 15 cell lines, these being BT20 and SKBR3. Both BT20 and SKBR3 are known to over-express this gene and this result is accurately reflected by the MT-PCR quantification results in the side-by-side quantitative comparison in FIG. 8. Information of this sort is of value in the treatment of patients with cancer and in some cases would provide the necessary information for the determination of suitable drug treatments.

TABLE 4

Tandem MT-PCR first round outer primers

| Gene | Forward | Reverse |
|---|---|---|
| ERBB2 | ACATGACCCCAGCCCTCTAC | AGAGAGTCTTGGCCCTTTCC |
| ESR1 | TGGAGATCTTCGACATGCTG | GCCATCAGGTGGATCAAAGT |
| EGFR | CTTGCAGCGATACAGCTCAG | GGTCCTGGTAGTGTGGGTCT |
| TOP2A | GCTGATGATGTTAAGGGCAGT | GATTCTTGGTTTTGGCAGGA |
| CCND1 | TCCTCTCCAAAATGCCAGAG | TGAGGCGGTAGTAGGACAGG |
| PTEN | CAGTCAGAGGCGCTATGTGT | AGGTAACGGCTGAGGGAACT |
| CDH1 | AGCGTGTGTGACTGTGAAGG | CTCTTCTCCGCCTCCTTCTT |
| CDKN1A | CCATGTGGACCTGTCACTGT | AAGATGTAGAGCGGGCCTTT |
| MDM2 | GAAGGAAACTGGGGAGTCTTG | TTTTTGTGCACCAACAGACTTT |
| BTF3 | CCTTATTCGCTCCGACAAGA | TGGATCACTGTTCCTTGGTTT |
| RPL35 | AAGGAGGAGCTGCTGAAACA | GCATGGCACGTGTCTTCTTA |
| VEGF | GAGCGGAGAAAGCATTTGTT | GGAGGCTCCTTCCTCCTG |
| TP53 | CTTCGAGATGTTCCGAGAGC | TCTGAGTCAGGCCCTTCTGT |
| MYC | CCTACCCTCTCAACGACAGC | CTCTGACCTTTTGCCAGGAG |
| PgR | TGGTGTTTGGTCTAGGATGGA | AGCCCTTCCAAAGGAATTGT |
| BSG | TGCTGGTCTGCAAGTCAGAG | GCCTCCATGTTCAGGTTCTC |
| MKI67 | AGCAACCGCAGTTGACAAG | GGGCGTTTTGCTACGTTT |
| GSTM3 | TTGGAAGAGCTACCTGGACAA | CGATTTTCTCCAAAGCCTCA |
| GEM | CTTCGAGAAGGCATCTGAGC | CCCTCAAACAGCTCCTTCAC |
| MELK | AAAGGGGTTGGATAAGGTT | TGCATTGTCACTTTCCCAAA |
| MAD2L1 | TGTGGTGGAACAACTGAAAG | TGGCAGAAATGTCACCGTAG |
| BUB1 | CAGCAAAGTGTGAAACATCTGG | TCCACATATCCAAATGAGGAAG |
| TPD52 | GAGATCAAGCGGAAACTTGG | TTCCAGCTTTTTGGTGATGA |
| HPRT | GACCAGTCAACAGGGGACAT | TTTCAAATCCAACAAAGTCTGG |

TABLE 5

Tandem MT-PCR second round inner primers

| | Forward primer | Reverse primer |
|---|---|---|
| ERBB2 | GTACCCCTGCCCTCTGAGAC | CGAACATCTGGCTGGTTCAC |
| ESR1 | GATGAATCTGCAGGGAGAGG | TCCAGAGACTTCAGGGTGCT |
| EGFR | TCCTCCCAGTGCCTGAATAC | GGGTTCAGAGGCTGATTGTG |
| TOP2A | TGCTACACATTTCCCAGATGA | CGGTAGTGGAGGTGGAAGAC |
| CCND1 | GCGGAGGAGAACAAACAGAT | GGCGGATTGGAAATGAACT |
| PTEN | TGGCACTGTTGTTTCACAAG | TCACCTTTAGCTGGCAGACC |
| CDH1 | ATTGCAAATTCCTGCCATTC | CAGCAAGAGCAGCAGAATCA |
| CDKN1A | GACTCTCAGGGTCGAAAACG | GGATTAGGGCTTCCTCTTGG |
| MDM2 | GAGCAGGCAAATGTGCAATA | AAGCAATGGCTTTGGTCTAA |
| BTF3 | CAGGAAAAACTCGCCAAACT | TCATCTGCTGTGGCTGTTCT |
| RPL35 | GACCTGAAGGTGGAGCTGTC | ACTGTGAGAACACGGGCAAT |
| VEGF | CAAGATCCGCAGACGTGTAA | TCACATCTGCAAGTACGTTCG |
| TP53 | GGAGCACTAAGCGAGCACTG | CACGGATCTGAAGGGTGAAA |
| MYC | TGCTCCATGAGGAGACACC | CCTGCCTCTTTTCCACAGAA |
| PgR | GTCAGTGGGCAGATGCTGTA | TGCCACATGGTAAGGCATAA |
| BSG | TGGGCCTGGTACAAGATCAC | GCGAGGAACTCACGAAGAAC |
| MKI67 | CCCCACCTCAGAGAGTTTTG | GGGCTTGCAGAGCATTTATC |
| GSTM3 | GGGAAATTCTCATGGTTTGC | CAGGCACTTGGGGTCAAATA |
| GEM | TGGTTGGCAACAAAAGTGAC | ACAGCTGCAGAGGTCTCGAT |
| MELK | GGAGCAAAAGGAAGGGTTCT | CAACAGTTGATCTGGATTCACTAA |
| MAD2L1 | TCCTGGAAAGATGGCAGTTT | CGGATTTCATCCTGGATAGC |
| BUB1 | CTCAGCAACAAACCATGGAA | GTGCCAAAGAGCATGCAATA |
| TPD52 | GCAAGACGTGACAGCAACAT | GAGCCAACAGACGAAAAAGC |
| HPRT | GCAGACTTTGCTTTCCTTGG | ACACTTCGTGGGGTCCTTTT |

Example 8

Figure 9A:
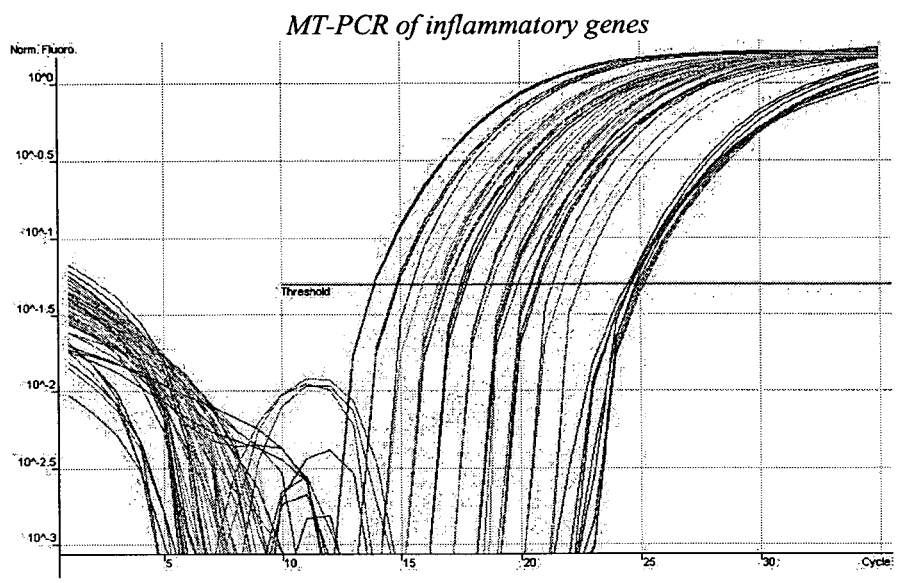
FIG. 9A. Quantification of inflammatory genes by MT-PCR showing the expression of 17 inflammatory genes in triplicate from a human skin biopsy.
Figure 9B:
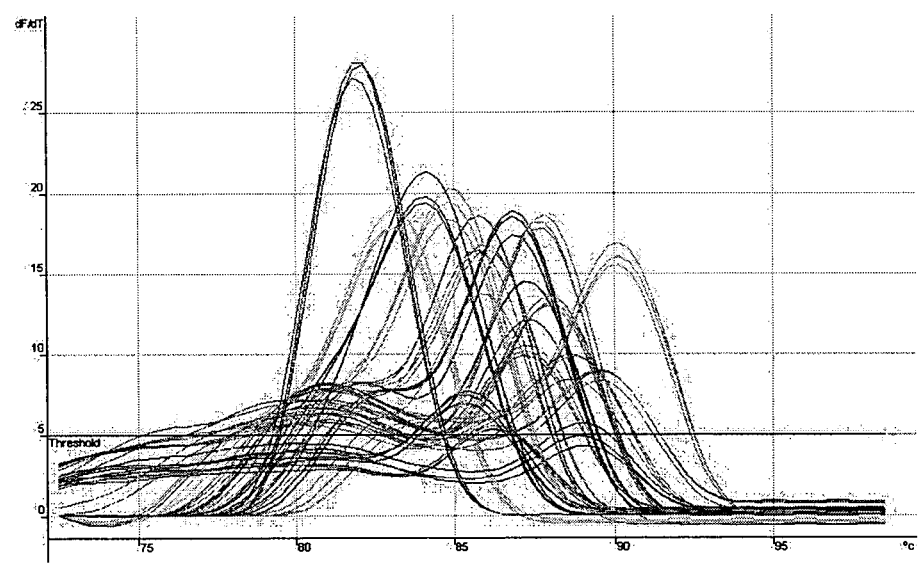
FIG. 9B. Corresponding melt curves for the amplification products of FIG. 9A.
Figure 9C:
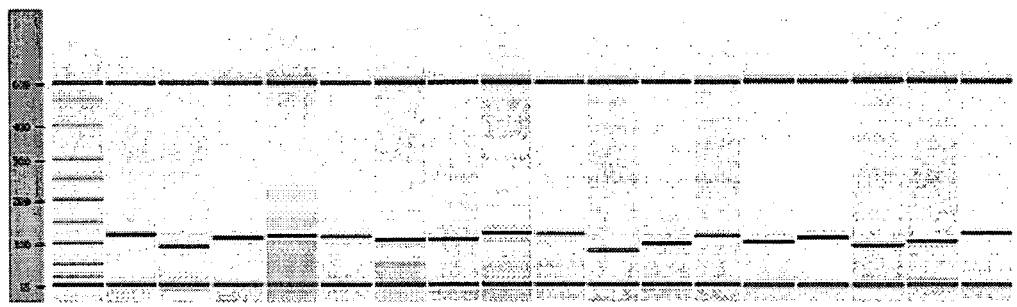
FIG. 9C. Bioanalyzer analysis of the amplification products of FIG. 9A.

MT-PCR has Wide Applicability to Any Gene that can be Measured by PCR: Quantification of Inflammatory Gene Expression Products in Endothelial Cells To demonstrate the further application of MT-PCR in other clinically relevant areas, the expression of 17 inflammatory genes was quantified from 100 ng of RNA isolated from a human skin biopsy and analysed using 10 cycles of multiplex amplification in the first round followed by 35 cycles of second round amplification. All 17 genes amplified in triplicate efficiently and accurately as shown in FIG. 9A. It will be noted that the triplicate measurements show that each gene expression product has been measured with high reproducibility. The corresponding melt curves shown in FIG. 9B also show that every second round amplification reaction resulted in a single product lacking contamination with non-specific products, primer dimer and the like, even after 35 cycles of amplification in the second round. The specificity of the amplification was further confirmed by analysis using a Bioanalyzer (Agilent Technologies) as shown in FIG. 9C, which clearly shows that single PCR products were present in each reaction. The genes used in this MT-PCR assay were validated by demonstrating that they produced a single product when assayed on their own in a standard PCR reaction. They were then used together in a highly multiplexed MT-PCR reaction previously optimised for a set of cancer-related genes without further optimisation. This example demonstrates that any PCR reaction that functions well when assayed on its own is likely to function in a substantially similar manner when incorporated in a highly multiplexed MT-PCR reaction without further optimisation.

Example 9

MT-PCR Combined with High Resolution-Melt Analysis for the Identification of Target Sequences The MT-PCR method can also be combined with high-resolution melt curve analysis for a wide variety of applications such as the identification of target DNA sequences, the detection of different viral or bacterial strains in heterogenous samples, the detection and quantification of SNPs, DNA methylation (after bisulfite treatment) and genotyping. Examples of melt curve analysis preferably utilising intercalating dyes that saturate the double stranded amplicon DNA such as SYTO9, EvaGreen or LCGreen include the detection of multiple virus strains (Varga, A and James, D (2006) *J. of Virol. Methods* 132:146-153), different bacterial species (Bell C A and Patel R. (2005) *Diagn Microbiol Infect Dis.* 53(4): 301-6), DNA methylation analysis (Worm et al., (2001) *Clinical Chemistry* 47:1183-1189) and mutation and genotyping analysis for cancer diagnostics (Bernard, P. S. and Wittwer, C. T (2002) *Clinical Chemistry* 48(8): 1178-1185; Powell B. L. et al., (2002) *Carcinogenesis* 23(2):311-315). High-resolution melt analysis clearly has wide applicability to any gene that can be measured by PCR.

Figure 10A:
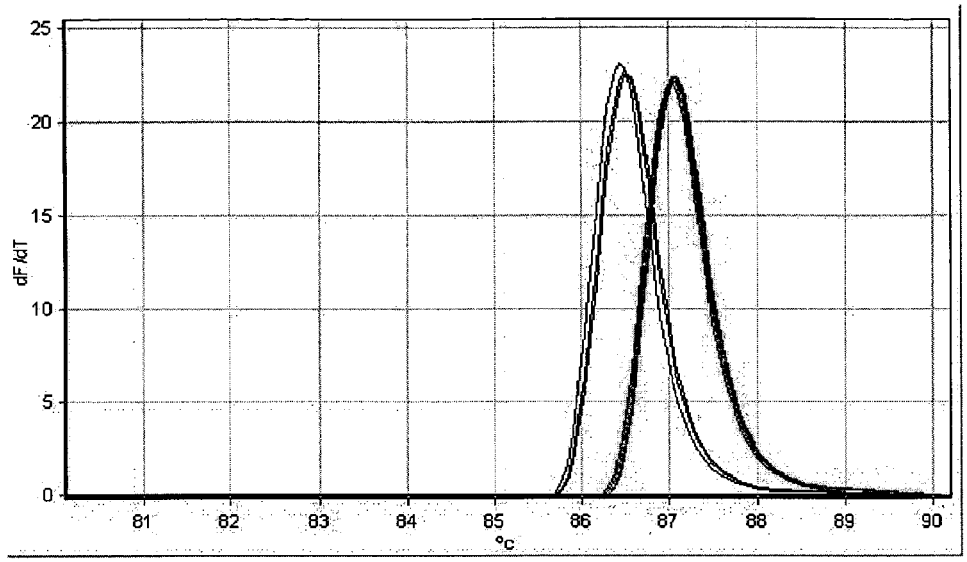
FIG. 10A. Analysis of hypervariable region of TP53 by high resolution melt in human breast cancer cell lines.
Figure 10B:
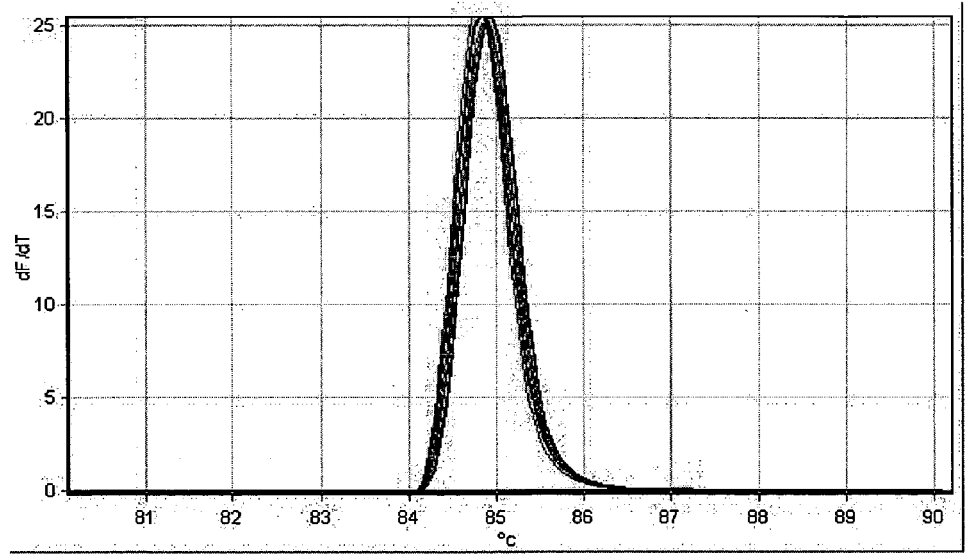
FIG. 10B. Analysis of a region of TP53 with no mutations using high resolution melt in human breast cancer cell lines.

To obtain a melt curve profile from an amplification reaction, which could contain one or multiple MT-PCR products, the product(s) are gradually heated from about 60° C. to about 95° C., wherein the fluorescent reporter, such as SYTO-9 dye, rapidly dissociates from the amplified products at the temperature at which the DNA changes from a double stranded form to a single stranded form causing a drop in emitted fluorescence at a characteristic temperature. This change in fluorescence is monitored continuously or regularly across the temperature gradient and the change in fluorescence is then plotted along a temperature gradient axis to obtain the melt curve profile. As each specific target PCR product has a specific melting temperature (Tm), these may be identified by their differing melting temperatures as demonstrated in FIGS. 10A and 10B. The precise temperature control of the Rotor-gene 6000 (Corbett Research) allows melt temperatures to be determined with an accuracy of less than 0.02° C. This is sufficient to distinguish small mutations in targets amplified by MT-PCR or to confirm that the correct target has been amplified in the reaction. In FIG. 10A, a region of the TP53 gene, which is susceptible to mutation, was amplified by MT-PCR from 8 samples selected from two human breast cancer cell lines and analysed by high resolution melt on the Rotor-gene 6000. It can be seen that the amplification products from the SKBR3 cell line displays a mutant TP53 gene region (with a melt temperature of 86.46° C.) and that this can easily be distinguished from amplification products of the MCF7 cell line having a wild-type TP53 gene region (with a melt temperature of 87.16° C.). Since some hypervariable motifs in the TP53 gene are known to have therapeutic consequences, this analysis and others like it can be of use in predictive medicine as also discussed in Powell et al., (supra). FIG. 10B shows a comparative study on a region of the TP53 gene that does not display such mutations. This region was also amplified using MT-PCR on samples taken from the two cell lines. In this case, the curves indicate that the MT-PCR amplification products from both SKBR3 and MCF7 are the same, having the same melt temperature of 84.90° C. It should be additionally noted that it is advantageous to optimise the second round amplification reaction components to improve the accuracy and reliability of the melting curve profiles and, in this regard, it is frequently beneficial if DMSO is not included in the second round amplification mixture.

Example 10

MT-PCR Combined with High Resolution-Melt Analysis for Bacterial Identification

Figure 11A:
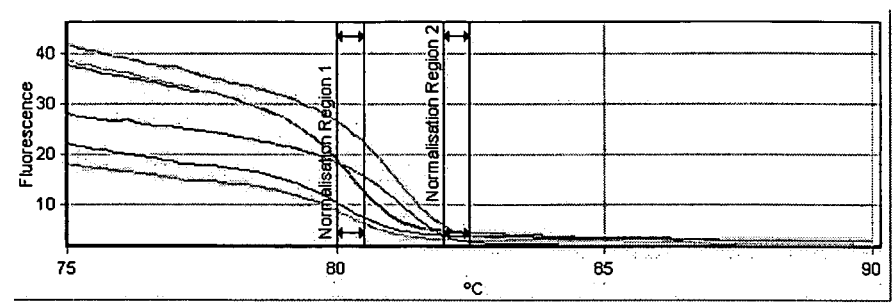
FIG. 11A. Analysis of 16S RNA amplicon in various bacterial strains by high resolution melt.
Figure 11B:
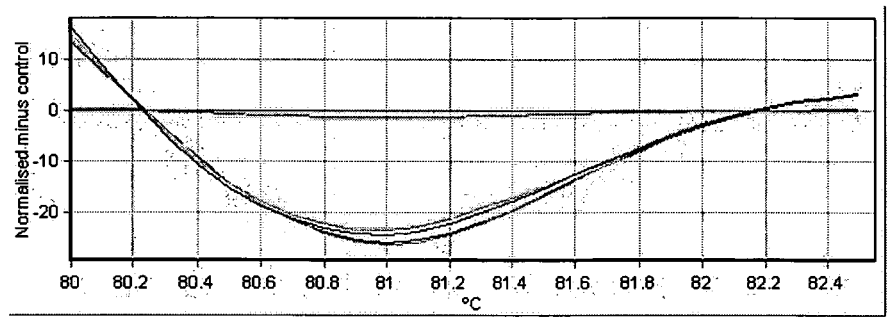
FIG. 11B. Difference plot of normalised melt curve shown in FIG. 11A.

The high-resolution melt curve analysis method, as described in Example 9, was again used, but a comparator DNA sample was provided, such that the test DNA could be compared with the comparator DNA after normalisation of the melt curves to give a highly sensitive measurement of identity or dissimilarity with the comparator. In FIGS. 11A and 11B, the melt curves of a number of bacterial DNA extracts is shown after amplification with primers specific for the 16S rRNA gene of *Enterococcus*. The similarity with the 16S sequence of other bacteria means that these too will generate a PCR product, even after nested amplification by MT-PCR. After normalisation of the melt curves between the regions shown in FIG. 11A, one melt curve was identified as a genuine *Enterococcus* melt curve and all the other melt curves compared with it (FIG. 11B). In this figure the horizontal lines are from the comparator *Enterococcus* and another sample of *Enterococcus* that is identified with a 98% confidence. The other melt curves are shown to be different bacteria as they have a very low level of confidence that they could be *Enterococcus* (Table 5). MT-PCR is particularly suited to high resolution melt analysis as the purity of the products improves the reliability of results. Furthermore, for forensic analysis the sensitivity of MT-PCR is well suited to analysis of traces of human tissue, and for tissue typing the large number of targets that may be simultaneously determined makes the method very accurate.

TABLE 5

| Sample | Genotype | Confidence % |
| --- | --- | --- |
| *Enterococcus* (comparator) | *Enterococcus* | 100 |
| *Staphylococcus* | Variation | 0.62 |
| *Enterobacteriacea* | Variation | 0.26 |
| *Streptococcus* | Variation | 0.23 |
| *Staphylococcus* | Variation | 0.38 |
| *Enterococcus* | *Enterococcus* | 98.28 |

It will be appreciated by one skilled in the art that the MT-PCR method and the MT-PCR method including or combined with high resolution melt curve analysis may be carried out using a range of thermocycler platforms and detection systems including a range of fluorescent reporters. For example, while the amplification reactions and melt curve analysis may be carried out using the Rotor-gene 6000, this may also be achieved using other systems such as the Light cycler® (Roche), the ABI PRISM® 7000, 7700 and 7900 (Applied Biosystems), the SmartCycler® (Cepheid), iCycler™ (BioRad) and other such platforms as will be known to one skilled in the art. Accordingly, MT-PCR and MT-PCR including or combined with melt curve analysis may be carried out using a range of fluorescent reporters such as SYBR-green I, SYTO9, LC Green, EvaGreen, Lightcycler® probes, LUX™ fluorogenic Primers and the like as will be apparent to one skilled in the art.

Although the present invention has been described with reference to a number of preferred embodiments, the skilled addressee will appreciate that numerous variations and modifications are possible without departing from the scope of the invention.

The claims defining the invention are as follows:

1. A method of amplifying a plurality of selected nucleic acid molecules from a pool of nucleic acid molecules comprising:
   (a) amplifying a plurality of selected nucleic acid molecules in a first round multiplex reaction including a plurality of outer primer pairs, each pair being specific for a selected nucleic acid sequence, present in the reaction in excess relative to amplicons synthesized with said outer primer pairs, and not exhausted after said first round multiplex reaction;
   (b) diluting the amplicons and remaining reaction components from said first round multiplex reaction into a plurality of second round amplification reactions each including at least one pair of inner primers, each pair being specific for one of said selected nucleic acid sequences, wherein said dilution is at least a 20-fold dilution such that the amount of outer primers introduced into each of said second round amplification reactions is insufficient to impair the amplification of said selected nucleic acid molecules using said inner primers; and
   (c) further amplifying said selected nucleic acid molecules in said plurality of second round amplification reactions whereby each second round reaction further amplifies a subset of said plurality of selected nucleic acid molecules respectively from said inner primers.

2. A method according to claim 1 wherein said nucleic acid molecules include DNA molecules.

3. A method of amplifying a plurality of selected nucleic acid molecules according to claim 1 wherein said primers included in said second round amplification reaction have a higher Tm than at least one of said outer primers included in said first round amplification reaction, such that said oligonucleotide priming in said second round amplification reaction is substantially biased in favour of said printers having said higher Tm.

4. A method of amplifying a-plurality of selected nucleic acid molecules according to claim 1 wherein at least one of said outer primers includes UTP nucleotides whereby said primer is amenable to digestion by a UNG enzyme.

5. A method of amplifying a plurality of selected nucleic acid molecules according to claim 4 wherein said outer primers are removed at the end of said first round of amplification by digestion with a UNG enzyme thereby substantially preventing contamination of said second round amplification reaction by said first round primers.

6. A method according to claim 1 wherein the first round multiplex reaction is allowed to proceed for up to about 20 cycles.

7. A method according to claim 1 wherein the multiplex amplification reaction amplifies more than about 4 selected nucleic acid molecules.

8. A method according to claim 7 wherein the multiplex amplification reaction amplifies between about 4 and 150 selected nucleic acid molecules.

9. A method according to claim 8 wherein the multiplex amplification reaction amplifies between about 10 and 150 selected nucleic acid molecules.

10. A method according to claim 9 wherein the multiplex amplification reaction amplifies between about 20 and 100 selected nucleic acid molecules.

11. A method of amplifying a plurality of selected nucleic acid molecules according to claim 1, wherein the method is used in a method of detecting of polymorphisms, mutations, insertions and deletions.

12. A method of amplifying a plurality of selected nucleic acid molecules according to claim 1, wherein the method is used in a method of diagnosis of diseases and disorders.

13. A method according to claim 12, wherein the method is used for the diagnosis of a neoplasm.

14. A method according to claim 13 wherein said neoplasm is breast cancer.

15. A method according to claim 13 wherein said neoplasm is colorectal cancer.

16. A method according to claim 12, wherein said method includes melt curve analysis.

17. A method according to claim 16, wherein said melting curve is generated having a resolution in the range of about 0.05° C. to about 0.02° C.

18. A method according to claim 16, wherein said melting curve is generated having a resolution of less than 0.02° C.

19. A method of amplifying a plurality of selected nucleic acid molecules according to claim 1, wherein the method is used for the detection and identification of selected organisms.

20. A method according to claim 19 wherein said organisms are detected and identified by sequencing of said nucleic acid products.

21. A method according to claim 20 wherein said organisms are selected from the group of bacteria, viruses, fungi, mycoplasma, and parasites or combinations thereof.

22. A method according to claim 19 wherein said organisms are selected from the group of bacteria, viruses, fungi, mycoplasma, and parasites or combinations thereof.

23. A method according to claim 1 wherein the amplification reactions are automatically processed in a thermal cycling apparatus.

24. A method according to claim 23 wherein said thermal cycling apparatus is a multi-well real time thermal cycling apparatus.

25. A method according to claim 23 wherein said thermal cycling apparatus is a continuous flow PCR device.

26. A method according to claim 23 wherein said thermal cycling apparatus is a rotary thermal cycling apparatus.

27. A method of amplifying a plurality of selected nucleic acid molecules from a pool of nucleic acid molecules comprising:
(a) amplifying a plurality of selected nucleic acid molecules in a first round multiplex reaction including a plurality of first round primer pairs comprising outer primers, each pair being specific for a selected nucleic acid sequence, present in the reaction in excess relative to amplicons synthesized with said outer primer pairs, and not exhausted after said first round multiplex reaction;
(b) diluting the amplicons and remaining reaction components from said first round multiplex reaction into a plurality of second round amplification reactions each including at least one pair of second round primers, each pair comprising an inner primer and one of said outer primers and being specific for one of said selected nucleic acid sequences, wherein said dilution is at least a 20-fold dilution such that the amount of outer primers introduced into each of said second round amplification reactions is insufficient to impair the amplification of said selected nucleic acid molecules using said second round primers; and
(c) further amplifying said selected nucleic acid molecules in said plurality of second round amplification reactions whereby each second round reaction further amplifies a subset of said plurality of selected nucleic acid molecules respectively from said second round primers.

28. A method of estimating the number of selected nucleic acid molecules from a pool of nucleic acid molecules comprising:
(a) amplifying a plurality of selected nucleic acid molecules in a first round multiplex reaction including a plurality of outer primer pairs, each pair being specific for a selected nucleic acid sequence, present in the reaction in excess relative to amplicons synthesized with said outer primer pairs, and not exhausted after said first round multiplex reaction;
(b) diluting the amplicons and remaining reaction components from said first round multiplex reaction into a plurality of second round amplification reactions each including a detectable reporter and at least one pair of inner primers, each pair being specific for one of said selected nucleic acid sequences, wherein said dilution is at least a 20-fold dilution such that the amount of outer primers introduced into each of said second round amplification reactions is insufficient to impair the amplification of said selected nucleic acid molecules using said inner primers; and
(c) further amplifying said selected nucleic acid molecules in said plurality of second round amplification reactions whereby each second round reaction further amplifies a subset of the plurality of selected nucleic acid molecules respectively from said inner primers; and
(d) monitoring each second round amplification reaction by means of said detectible reporter such that the number of selected nucleic acid molecules of each selected sequence is estimated.

29. A method of estimating the number of selected nucleic acid molecules from a pool of nucleic acid molecules according to claim 28 wherein said detectible reporter is a dye that intercalates double stranded DNA or interacts with single stranded DNA.

30. A method of estimating the number of selected nucleic acid molecules from a pool of nucleic acid molecules according to claim 28 wherein said second round amplification reaction includes a plurality of primer pairs and a plurality of fluorogenic probes such that a plurality of selected nucleic acid molecules of each selected sequence is amplified and quantified.

31. A method of estimating the number of selected nucleic acid molecules from a pool of nucleic acid molecules comprising:
(a) amplifying a plurality of selected nucleic acid molecules in a first round multiplex reaction including a plurality of outer primer pairs, each pair being specific for a selected nucleic acid sequence, present in the reaction in excess relative to amplicons synthesized with said outer primer pairs, and not exhausted after said first round multiplex reaction;
(b) diluting the amplicons and remaining reaction components from said first round multiplex reaction into a plurality of second round amplification reactions each including a detectable reporter and at least one pair of second round primers, each pair comprising an inner primer and one of said outer primers and being specific for one of said selected nucleic acid sequences, wherein said dilution is at least a 20-fold dilution such that the amount of outer primers introduced into each of said second round amplification reactions is insufficient to impair the amplification of said selected nucleic acid molecules using said second round primers; and
(c) further amplifying said selected nucleic acid molecules in said plurality of second round amplification reactions whereby each second round reaction further amplifies a subset of said plurality of selected nucleic acid molecules respectively; and
(d) monitoring each second round amplification reaction by means of said detectible reporter such that the number of selected nucleic acid molecules of each selected sequence is estimated.

32. A method of estimating the number of selected nucleic acid molecules from a pool of nucleic acid molecules according to claim 31 wherein said detectible reporter is a dye that intercalates double stranded DNA or interacts with single stranded DNA.

33. A method of estimating the number of selected nucleic acid molecules from a pool of nucleic acid molecules according to claim 31 wherein said second round amplification reaction includes a plurality of primer pairs and a plurality of fluorogenic probes such that a plurality of selected nucleic acid molecules of each selected sequence is amplified and quantified.

* * * * *

UNITED STATES PATENT AND TRADEMARK OFFICE
CERTIFICATE OF CORRECTION

| | | |
|---|---|---|
| PATENT NO. | : 8,962,250 B2 | Page 1 of 1 |
| APPLICATION NO. | : 11/515377 | |
| DATED | : February 24, 2015 | |
| INVENTOR(S) | : Keith Stanley | |

It is certified that error appears in the above-identified patent and that said Letters Patent is hereby corrected as shown below:

On the Title Page, Item (54) and in the Specification, Column 1, Title should read: METHODS FOR THE AMPLIFICATION, QUANTITATION AND IDENTIFICATION OF NUCLEIC <u>ACIDS</u>

Signed and Sealed this
Sixteenth Day of June, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,962,250 B2 | Page 1 of 1 |
| APPLICATION NO. | : 11/515377 | |
| DATED | : February 24, 2015 | |
| INVENTOR(S) | : Keith Stanley | |

It is certified that error appears in the above-identified patent and that said Letters Patent is hereby corrected as shown below:

Title Page,

(73) Assignee should read: AusDiagnostics Pty Ltd., Alexandria (AU)

Signed and Sealed this
Fourteenth Day of June, 2016

Michelle K. Lee
*Director of the United States Patent and Trademark Office*